(12) United States Patent
Vess

(10) Patent No.: US 7,788,039 B2
(45) Date of Patent: Aug. 31, 2010

(54) QUANTITATION OF NUCLEIC ACIDS USING GROWTH CURVES

(75) Inventor: Thomas Vess, Raleigh, NC (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 899 days.

(21) Appl. No.: 10/946,904

(22) Filed: Sep. 21, 2004

(65) Prior Publication Data

US 2005/0118620 A1 Jun. 2, 2005

Related U.S. Application Data

(60) Provisional application No. 60/506,515, filed on Sep. 25, 2003.

(51) Int. Cl.
*G06F 19/00* (2006.01)
*C12Q 1/68* (2006.01)
*C12P 19/34* (2006.01)

(52) U.S. Cl. ........................................ 702/19

(58) Field of Classification Search ................ None
See application file for complete search history.

(56) References Cited

FOREIGN PATENT DOCUMENTS

EP 1 138 784 A 10/2001

WO WO03/067215 8/2003

OTHER PUBLICATIONS

Roche Applied Science Technical Note, vol. LC13, "Relative Quantification", 2001, XP002311958, http://www.roche-applied-science.com/lightcycler-online/lc_support/pdfs/lc_13.pdf, pp. 1-28.

Lightcycler Operator's Manual, "Lightcycler operator's manual, version 3.5", Oct. 2000, XP002966635, pp. 8-189.

Wilhelm, J. et al., "Validation of an algorithm for automatic quantification of nucleic acid copy numbers by real-time polymerase chain reaction", Analytical Biochemistry, vol. 317, No. 2, Jun. 15, 2003, XP002312097, ISSN: 0003-2697, pp. 218-225.

Quondam, M., et al. 1997, "Homology Modeling of *Neurospora crassa* Geranylgeranyl Pyrophosphate Synthase: Structural Interpretation of Mutant Phenotypes", Protein Engineering, vol. 10, 9:1047-1055.

*Primary Examiner*—Lori A Clow
(74) *Attorney, Agent, or Firm*—Fish & Richardson P.C.

(57) ABSTRACT

Methods, apparatus, and systems, including computer program products, implement techniques for determining an amount of target nucleic acid ("target") in a sample. Signal data is received for a plurality of cycles of an amplification experiment performed on the target and a standard nucleic acid ("standard"). The signal data includes a series of signal values indicating a quantity of standard present during cycles of the standard amplification, and a series of signal values indicating a quantity of target present during cycles of the target amplification. A target growth curve value is defined using the target signal values and a standard growth curve value is defined using the standard signal values. An initial amount of the target is calculated according to a calibration equation using an initial amount of the standard, and the target and standard growth curve values, where the calibration equation is a nonlinear equation.

33 Claims, 18 Drawing Sheets

QUANTITATION OF NUCLEIC ACIDS USING GROWTH CURVES

CROSS-REFERENCE TO RELATED APPLICATIONS

This application claims the benefit of U.S. Provisional Application No. 60/506,515, filed Sep. 25, 2003, which is hereby incorporated by reference in its entirety.

TECHNICAL FIELD

This invention relates to the quantitative analysis of nucleic acids.

BACKGROUND

Polymerase Chain Reaction (PCR) is a powerful and widely used technology for amplifying nucleic acid sequences. PCR uses a polymerase such as *Thermus aquaticus* (Taq) polymerase to replicate or amplify copies of a particular segment of a nucleic acid. The number of copies of the nucleic acid increases exponentially, at least initially, and then tapers off as reactants become limiting or otherwise interfere with replication.

Conventional PCR assays are used to amplify a nucleic acid in a sample for use in, for example, analyses such as genotyping that require relatively large amounts of material. Conventional PCR assays can also be used in clinical applications to detect the presence in a cell or tissue sample of a particular pathogen or protein—for example, to detect unique mRNA transcripts from abnormal cells in a background of normal cells.

For many diseases, a quantitative measurement is needed to make a proper diagnosis, such as when a pathogen is normally present, a gene is normally expressed at low levels, or a virus is maintained endogenously in a healthy cell or tissue. Precise quantitative measurements are needed, for example, to diagnose certain infectious diseases, cancers, and autoimmune diseases, and may be useful therapeutically to assess the response of a disease to treatment and make prognoses for recovery. Precise quantitative measurement may also help detect false positives, which can occur if there is any contamination of a sample.

It can be difficult, however, to quantitate the results of any particular PCR because data from separate experiments or amplifications are typically not comparable. Amplification is an exponential process, so small differences in any of the variables which affect the reaction rate—including the length and sequence of the primer pairs, the concentration of reactants such as template and nucleosides, and the conditions for the reaction—can lead to dramatic differences in the amplification and ultimate yield of PCR product. In short, every PCR will have different reaction dynamics.

Two general approaches have made it possible to control for much of the variability among PCRs and get quantitative or at least semi-quantitative data for nucleic acids: (1) co-amplification or "competitive" PCR and (2) modeling of PCR amplification or "growth curves."

Co-amplification is the amplification in the same mixture of two nucleic acids, such as a target nucleic acid ("target") and a standard nucleic acid ("standard"). By conducting the PCRs of the target and standard simultaneously and under the same conditions, the effect of variables such as those noted above can be controlled, since the target and standard undergo the same treatment and experience the same conditions. Ideally, the same primers are used to amplify the target and the standard, thereby controlling for differences in efficiency due to differences in the annealing of the primers.

The relative amount of two nucleic acids can be determined by using, for example, heterogeneous methods such as agarose gel electrophoresis, Northern blot analysis, or differential display. In a co-amplification assay, a known concentration, and hence a known quantity or amount, of standard can be added to a sample containing an unknown amount of target to form a mixture and the two nucleic acids are amplified. The quantity of target can then be approximated by comparing the amount of target and standard for various concentrations of sample. The concentration of standard for which there are similar amounts of target and standard product after amplification provides an estimate of the initial amount of target.

The development of various probes has made it possible to analyze a PCR product with homogeneous methods, in real-time—that is, as the reaction proceeds. For example, some existing technologies use sequence-specific oligonucleotides to detect a product at each PCR cycle by measuring fluorescence emission. The measurements of fluorescence correspond to the number of copies of the nucleic acid. For example, TaqMan® probes utilize energy transfer fluorescence methods, in which the probes are self-quenched until cleaved during the PCR nuclease assay. With real-time sampling of a PCR, a growth curve can be fit to measures of the relative amounts of a nucleic acid at various cycles. A calibration curve, created from amplification of known quantities of the nucleic acid, can then be used to quantify the initial amount of the nucleic acid. See U.S. Pat. No. 6,503,720, "Method for quantification of an analyte."

Different combinations of fluorescent dyes can be used to simultaneously monitor in real-time the co-amplification of nucleic acids, and the absolute amount of target can then be determined by creating a standard curve for the standard nucleic acid. The standard curve can be generated, for example, by plotting the amount of the standard produced by some cycle in a PCR against varying, but known, amounts present before amplification. See U.S. Pat. No. 5,476,774, "Quantitation of nucleic acids using the polymerase chain reaction."

Although co-amplification of nucleic acids allows direct comparison and monitoring of different products during PCR, thereby providing data for use in quantitation, it can introduce certain artifacts into the data. For example, competitive effects may mean that linear calibrations are not accurate. Even in non-competitive methods, a change in the annealing temperature during PCR can cause a change in fluorescence signal and hence a shift in the baseline, and random effects, such as bubbles in a sample, can cause spikes in output data. Failure to identify and remove or correct these artifacts and anomalous features of the data can lead to misinterpretations of the PCR. In particular, failure to correct anomalies can result in false positives, and failure to account for the artifacts of a co-amplification will significantly reduce the precision and accuracy of quantitation based on co-amplification PCR data.

SUMMARY

The invention provides techniques for quantitating target nucleic acids based on PCR growth curves of the target nucleic acid and a standard nucleic acid of known initial concentration.

In general, in one aspect, the invention provides methods and apparatus, including computer program products, implementing techniques for determining an amount of a target nucleic acid in a sample. The techniques include receiving signal data for a plurality of cycles of an amplification experiment performed on a target nucleic acid and a standard nucleic acid. The signal data include a series of standard signal values that indicate a quantity of the standard nucleic acid present during cycles of the signal amplification, and a series of target signal values that indicate a quantity of the target nucleic acid present during cycles of the target amplification. A target growth curve value is defined using the target signal values and a standard growth curve value is defined using the standard signal values. An initial amount of the target nucleic acid is calculated according to a calibration equation using an initial amount of the standard nucleic acid and the target and the standard growth curve values, where the calibration equation is a nonlinear equation.

Advantageous implementations can include one or more of the following features. The target growth curve value and the standard growth curve value can be defined by defining a baseline for a standard or target growth curve using a subset of the standard signal values or a subset of the target growth curve values, respectively, and normalizing the corresponding signal data with respect to the baseline. Defining a baseline can include identifying one or more dips or spikes in the signal data, and excluding one or more data value corresponding to the one or more dips or spikes from a set of data to be used to define the baseline. Identifying one or more spikes can include identifying a first order difference between adjacent data points and two or more second order differences for the adjacent data points, and confirming a spike if there is a first difference larger than a predefined SPAMP value and a change in sign of the second-order differences.

Defining a target growth curve value and a standard growth curve value can include determining an elbow value for the standard nucleic acid or the target nucleic acid, the elbow value representing a cycle of the standard or target amplification, respectively, in the elbow region of the standard or target amplification, respectively. Determining an elbow value for the standard nucleic acid or the target nucleic acid can include: determining a cycle of the standard or target amplification where the standard or target signal has a predefined signal value; determining a standard elbow value for the standard nucleic acid and a target elbow value for the target nucleic acid; determining the elbow value from the respective standard or target growth curve; and interpolating between a number of a cycle for which the standard or target signal, respectively, is less than the predefined signal value and a number of a cycle for which the standard or target signal, respectively, is greater than the predefined signal value. The elbow value can be a fractional cycle number.

The calibration equation can be derived from target growth curve values and standard growth curve values from a series of amplification experiments performed on known quantities of the target nucleic acid and a known quantity of the standard nucleic acid. The calibration equation can relate the initial amount of the target nucleic acid to the known quantity of the standard nucleic acid using the target and standard growth curve values. The calibration equation can be defined by plotting a correlate of the initial amount of the target nucleic acid against a function of the known quantity of the standard nucleic acid and the target and standard growth curve values to produce a calibration plot, and fitting a curve to the calibration plot. The function of the known quantity of the standard nucleic acid and the target and standard growth curve values can be a function of the difference between the target and standard growth curve values. Fitting a curve to the calibration plot can include fitting a second-order nonlinear curve to the calibration plot. The nonlinear can be defined by the formula: $T_o = Q_o \, 10^{a(n_Q - n_T)^2 + b(n_Q - n_T) + c}$, where $T_o$ is the initial amount of the target nucleic acid, $Q_o$ is the initial amount of the standard nucleic acid, $n_Q$ is the cycle number at which the quantity of standard nucleic acid is Q, and $n_T$ is the cycle number at which the quantity of standard is T.

The techniques can include checking the target signal values or the standard signal values for a dip, spike, drift, or step, and adjusting the target signal values or standard signal values, respectively. Adjusting the target signal values or standard signal values can include reporting that data is inadequate for calculating an initial amount of the target nucleic acid. Adjusting the target signal values or standard signal values can include deleting data values corresponding to the dip, spike, drift, or step.

In general, in another aspect, the invention provides methods and apparatus, including computer program products, implementing techniques for determining an amount of a target nucleic acid in a sample. The techniques include amplifying a known quantity of a standard nucleic acid and a sample of the target nucleic acid in successive cycles of a standard amplification and a target amplification, respectively, monitoring a standard signal that is indicative of a quantity of the standard nucleic acid and a target signal that is indicative of a quantity of the target nucleic acid to produce standard growth data and target growth data, defining a standard value from the standard growth data characterizing the standard amplification and a target value from the target growth data characterizing the target amplification, and determining the amount of the target nucleic acid using a nonlinear calibration equation and parameters for the calibration equation that relate a quantity of the target nucleic acid to the known quantity of the standard nucleic acid using the target and the standard values.

Advantageous implementations can include one or more of the following features. Amplifying a known quantity of a standard nucleic acid and a sample of the target nucleic acid can include combining the known quantity of a standard nucleic acid and the sample of the target nucleic acid to form a mixture; and co-amplifying the standard nucleic acid and the target nucleic acid in the mixture. Co-amplifying the standard nucleic acid and the target nucleic acid can include using a common pair of primers. The standard signal can be a first fluorescence signal and the target signal can be a second fluorescence signal. Monitoring a standard signal or a target signal can include monitoring a fluorescence signal derived from one of a pair of fluorescent dyes. Monitoring the standard or target signal can include monitoring the annealing of an oligonucleotide probe to the interior of the standard or target nucleic acid, respectively.

In general, in another aspect, the invention provides methods and apparatus, including computer program products, implementing techniques for defining a calibration equation for a target nucleic acid. The techniques include performing a series of amplification experiments using known quantities of a target nucleic acid and a known quantity of a standard nucleic acid and for each amplification experiment and receiving signal data for a plurality of cycles. The signal data can include a series of standard signal values indicative of quantities of the standard nucleic acid present during cycles of the signal amplification, and a series of target signal values indicative of quantities of the target nucleic acid present during cycles of the target amplification. Amplification data for the amplification experiment including a target growth curve value is defined using the target signal values. A standard growth curve value is defined using the standard signal values and an initial quantity of the target nucleic acid. A nonlinear calibration equation is defined that describes the initial quantity of the target nucleic acid in an amplification experiment as a function of the target and standard growth curve values for the amplification experiment using the amplification data for the amplification experiments.

In general, in another aspect, the invention provides methods and apparatus, including computer program products, implementing techniques for evaluating a target nucleic acid in a sample. The techniques include receiving signal data for a plurality of cycles of an amplification experiment performed on a target nucleic acid and a standard nucleic acid. The signal data includes a series of standard signal values indicative of quantities of the standard nucleic acid present during cycles of the signal amplification, and a series of target signal values indicative of quantities of the target nucleic acid present during cycles of the target amplification. The target signal values and the standard signal values are checked for an anomaly, and the target signal values and standard signal values are adjusted to account for the anomaly. A target growth curve value is defined using the target signal values and a standard growth curve value is defined using the standard signal values. The target nucleic acid is evaluated using the target and the standard growth curve values. The anomaly can be a dip, spike, step or drift.

In general, in another aspect, the invention provides a kit for determining an amount of a target nucleic acid in a sample. The kit includes a known quantity of a standard nucleic acid for use in successive cycles of a co-amplification with the target nucleic acid and hybridization probes for use in monitoring a standard signal that is indicative of a quantity of the standard nucleic acid and a target signal that is indicative of a quantity of the target nucleic acid to produce standard growth data and target growth data. The kit also includes a computer program product for defining a standard value from the standard growth data characterizing the standard amplification and a target value from the target growth data characterizing the target amplification. The kit also includes calibration data for determining the amount of the target nucleic acid using a nonlinear calibration equation, the calibration data including parameters for the calibration equation that relate a quantity of the target nucleic acid to the known quantity of the standard nucleic acid.

The invention can be implemented to provide one or more of the following advantages. Accurately characterizing growth curves makes it possible to establish accurately and precisely the quantity of a target nucleic acid in a sample prior to its amplification. Quantitation of a target nucleic acid can be automated. Data that are insufficient for quantitation can be identified. PCR growth curves can be checked for anomalies such as spikes and baseline shifts. Anomalies such as spikes and baseline shifts can be corrected. Data from the exponential phase of the PCR can be used effectively to quantitate a target nucleic acid. The algorithm modules use data from quantitative analysis of co-amplification PCR but can be applied in other contexts, such as genotyping and qualitative tests.

The details of one or more embodiments of the invention are set forth in the accompanying drawings and the description below. Unless otherwise defined, all technical and scientific terms used herein have the meaning commonly understood by one of ordinary skill in the art to which this invention belongs. All publications, patent applications, patents, and other references mentioned herein are incorporated by reference in their entirety. In case of conflict, the present specification, including definitions, will control. Other features and advantages of the invention will become apparent from the description, the drawings, and the claims.

DESCRIPTION OF DRAWINGS

Like reference symbols in the various drawings indicate like elements.

DETAILED DESCRIPTION

The methods and apparatus described herein provide for accurate and precise characterization of growth curves or growth curve values for a nucleic acid. The methods and apparatus also provide for quantitation of a target nucleic acid ("target") by characterizing the PCR growth curves or growth curve values of the target and a standard nucleic acid ("standard") of known initial concentration, and provide for measurements of the concentration of the target to be calibrated against the concentration of the standard using information from the growth curves of known concentrations of the target and the standard.

Figure 1:
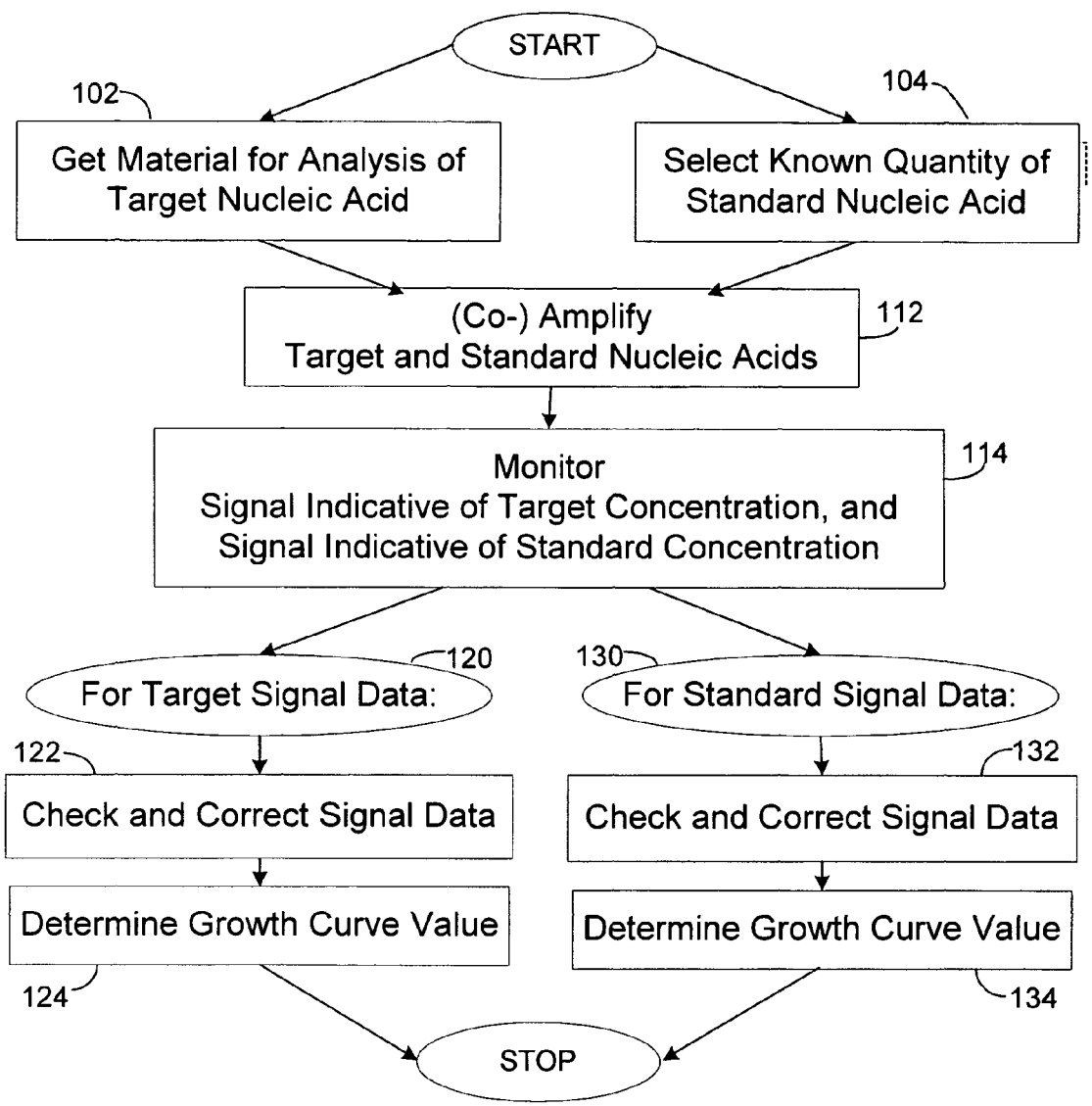
FIG. 1 is a flow diagram illustrating a method for characterizing growth curves and determining a growth curve value for a target nucleic acid and a growth curve value for a standard nucleic acid according to one aspect of the invention.

As shown in FIG. 1, the method begins (step 102) with material that is to be analyzed to determine the concentration of a target nucleic acid. The presence or quantity of target nucleic acid in the sample is usually not known. Typically, the material is derived from a biological sample, such as a blood or tissue sample. The material is prepared for analysis using conventional techniques. For example, the target nucleic acid can be extracted from the sample material manually or by an instrument built for sample-preparation. One or more target nucleic acids can be identified.

A standard nucleic acid is selected (step 104). The standard nucleic acid is typically selected so that it can be amplified using the same pair of primers that are used to amplify the target nucleic acid. The standard nucleic acid is typically synthesized using any of various conventional methods for designing DNA sequences. The standard can be a nucleic acid that is not naturally occurring or is otherwise non-conventional. For example, the standard may be a modified form of a naturally occurring nucleic acid. The standard can be modified to adjust its melting temperature, for example, by inserting TM modifier sequences. The standard also can be modified to remove carbohydrate moities, for example, by changing nucleotides that otherwise produce glycosylation signals. The concentration of the standard nucleic acid is known, or the quantity of standard nucleic acid can otherwise be determined.

The standard and target nucleic acids can be DNA (including genomic or viral DNA) or RNA (including viral RNA or mRNA). A target or standard that is DNA can be amplified or co-amplified using any of various conventional PCR methods. A target or standard that is RNA can be amplified or co-amplified using reverse transcript PCR (RT-PCR), whereby the RNA is first converted to DNA using reverse transcriptase, and PCR is then used to amplify the DNA. See McPherson, M. J., and S. G. Moller, *PCR: The Basics from Background to Bench*, Chapter 8: *Analysis of Gene Expression* (2000). RT-PCR makes it possible to measure gene expression, by sampling mRNA, and to detect retroviruses such as HIV. The standard nucleic acid can be combined with a sample of the material to be analyzed for the target nucleic acid (a sample of the target) and the resulting combination of standard and target sample can be co-amplified (step 112). Alternatively, each amplification can proceed separately under conditions that are as similar as possible.

The amplification of each of the nucleic acids is monitored (step 114) by measuring a signal indicative of the nucleic acid concentration or amount. The signal measurements thus correspond to the concentration or quantity of the nucleic acid present in the PCR at the time of measurement. Signal measurements are made at two or more times during the PCR. Thermal cyclers control the PCR conditions for a set (batch) of samples, and the temperatures and times of temperature changes are typically specified in a PCR profile. Such a profile can be used to control monitoring of the PCR, as well. For example, measurements can be taken at each cycle, for example, following denaturation or during amplification, or at intervals during the PCR.

If the target nucleic acid is co-amplified with the standard, the products of both PCRs can be simultaneously monitored in step 114 as the amplification proceeds. Such "on-line" or "real-time" detection of two or more amplification products is possible with systems such as any of the COBAS TaqMan® systems, and is described in more detail below.

In one implementation, the PCR is monitored by measuring at each cycle the fluorescence of labeled oligonucleotide probes that fluoresce under specified conditions, such as upon binding to the PCR product or until the PCR product is copied. Measurements of fluorescence are typically made after briefly illuminating the sample with filtered light (a "light" reading). To control for background effects and variability due to perturbations such as fluctuations in the instrument's sensitivity, the intensity of the light source can be measured as a reference ("reference") and data can be collected to characterize the background ("dark") level of fluorescence. The background is measured without illumination—for example, just before a sample is illuminated. Ideally, a background ("dark") level of fluorescence is determined for each fluorescence ("light") reading. The background level of fluorescence can be characterized as an average of multiple measurements, and may take into account any drift or variance in those readings. A corrected fluorescence signal, F, can then be determined as:

$$f = \frac{\text{Light} - \text{Dark}}{\text{Reference}} \tag{1}$$

While the invention is described here as using measurements of fluorescence, measurements of other signals may be used. Signals that indicate or correspond to the concentration of the PCR product are preferred. Ideally, the signal can be measured repeatedly and non-destructively for a sample, thereby allowing a PCR of the sample to be monitored as the PCR progresses.

Monitoring the signal indicative of the concentration of target nucleic acid produces a set of signal data for the target (120), and monitoring the signal indicative of the concentration of standard nucleic acid produces a set of signal data for the standard (130). The target data and the standard data can be stored, such as in a database.

Each set of signal data (120, 130) can represent a growth curve for the amplification of a nucleic acid, and is processed separately but similarly (steps 122, 124; 132, 134), as described in more detail below. In brief, in steps 122 and 132, the target and signal data, respectively, are checked for anomalies such as spikes, dips, steps, and baseline shifts. If such anomalies exist, they can be corrected. In steps 124 and 134, the corrected target and signal data are each evaluated in order to determine a growth curve value such as an "elbow value," which is the number or fractional number of a cycle where the amplification is in the elbow region of the amplification or growth curve, as explained in more detail below. An elbow value can be, for example, the cycle where the amplification produces an indicator of the quantity of the nucleic acid that is closest to a predefined value. An elbow value can be determined from a measure or calculation reflecting the shape of the growth curve, or from interpolation between observed values, as explained in more detail below.

Figure 2:
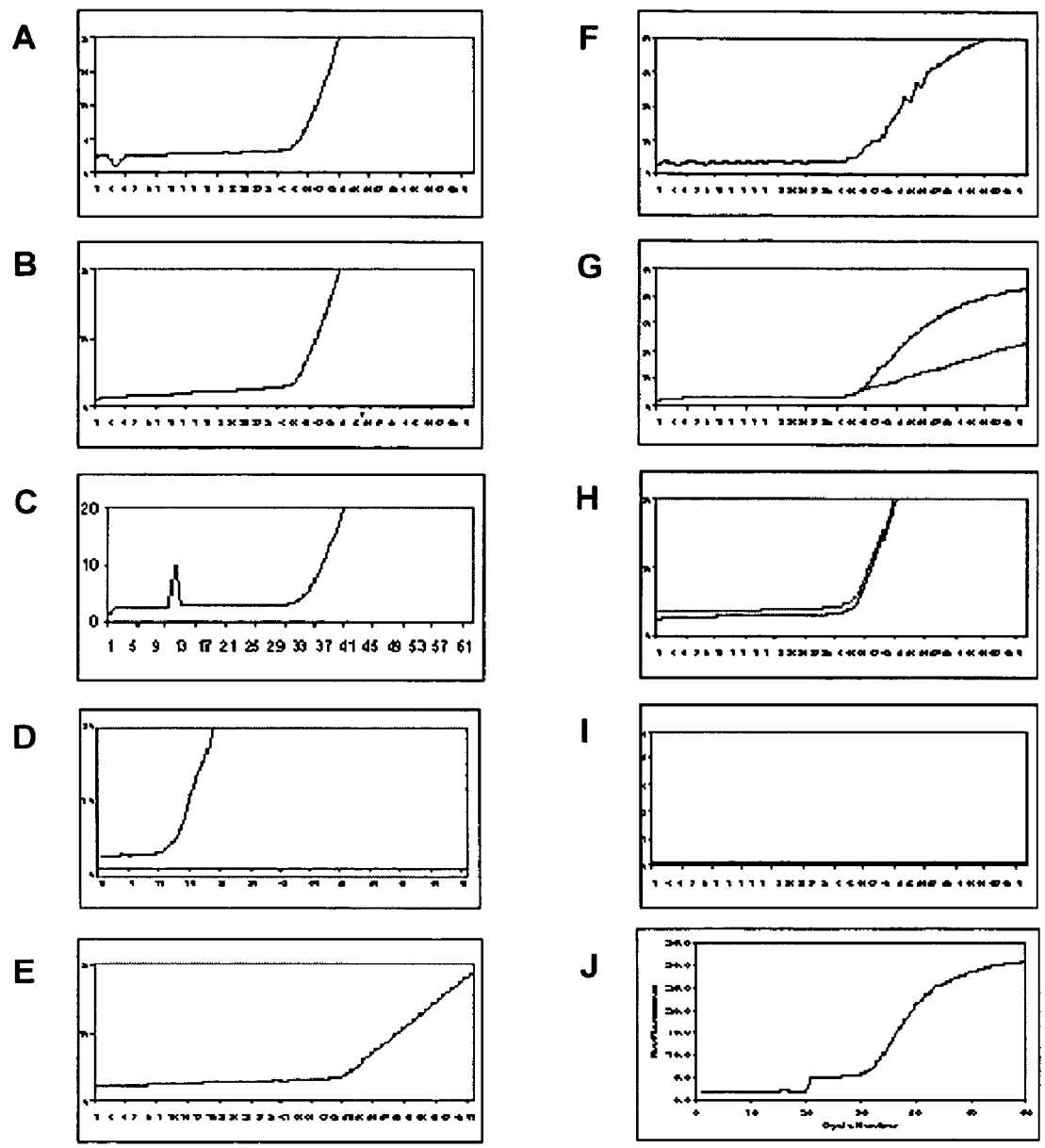
FIGS. 2A-J are plots illustrating exemplary PCR growth curves.

The signal data 120, 130 can be plotted as a function of the amplification cycle number to generate a growth curve. Amplification of a nucleic acid by PCR is an exponential process, so a PCR growth curve is typically and generally exponential in form, at least during the initial stages of a PCR. FIGS. 2A-J illustrate examples of growth curves that can be obtained in PCR experiments according to the method of FIG. 1. FIGS. 2A-D and H show growth curves that are generally exponential in form. The curve can be characterized by a high rate of amplification, as shown in FIG. 2D, or a low rate of amplification, as shown in FIG. 2E. PCRs that have high rates of amplification tend to have short (or no) baselines and a rapidly rising growth curve. PCRs that have low rates of amplification tend to have long baselines and slowly rising growth curves. In the latter case, growth may appear to be linear.

A growth curve may taper off after some period of exponential increase, as shown in FIG. 2F, G, J. However, each growth curve typically has an absolute baseline level, where the concentration or amount of product increases slowly if at all, as shown in FIGS. 2A-H, J. Each growth curve also typically has an "elbow," a region where the concentration or amount of product begins to increase rapidly, as also shown, for example, in FIGS. 2A-H, J.

Growth curves are generally smooth and increasing, but periodic or random signal changes may be superimposed on the signal data, producing a "noisy" curve as shown in FIG. 2F. A complete system failure can produce a "flat line" curve, as shown in FIG. 2I. Alternatively, where a PCR does proceed, there may be recognizable anomalies in the growth curve. Such anomalies can occur, for example, as a result of artifacts of the methodology, the behavior of the instrument, or random error. They can include, for example, baseline dips, baseline drift, signal spikes, and signal steps.

FIG. 2A shows a baseline dip, which typically occurs, if at all, during the first 5 to 10 amplification cycles. A baseline dip includes any anomalous rise or fall in signal. For example, a baseline dip can be "U"-like because the signal drops and then rises, as shown in FIG. 2A. A baseline dip can also be, for example, a rise followed by a fall, or any series of rises and falls. Baseline dips can result from inhomogeneities in the sample (e.g., incomplete mixing during preparation).

FIG. 2B shows baseline drift—a gradual upward (as shown) or downward slope in the growth curve that typically occurs prior to any notable increase in the signal. Baseline drift can be caused by changes or degradations in the sample during successive PCR cycles.

FIG. 2C shows a signal spike, which can occur anytime during the PCR, in which the signal changes suddenly and dramatically, jumping up or down. Signal spikes can be caused by inhomogeneities in the sample (e.g., bubble formation) or interference with the instrument or signal (e.g., cosmic rays on the detector). FIG. 2J shows a signal step, which changes the signal so that the growth curve is shifted up, as shown, or down. A signal step (shift) can occur anytime during the PCR, but is usually associated with a change in annealing temperature. For example, a fluorescence signal may be sensitive to temperature, such that the strength of the fluorescence changes with a change in annealing temperature.

In steps 122 and 132, target and standard data, respectively are checked for anomalies, and the anomalies can be corrected. Failure to identify and remove or correct signal anomalies can result in quantitative errors and incorrect results. Ideally, spikes, dips, or drift are identified and the spurious data removed or replaced with data that is consistent with smooth growth. Also ideally, baseline steps are identified and the data are adjusted to account for the shift. Data can also be checked against quality-control standards. Data that, for example, reflect a process failure, or have excessive noise or baseline slope, can be excluded from analysis. Co-amplification of nucleic acids can increase the likelihood of observing anomalies in PCR growth curve data and can limit the range of usable data. For example, inhomogeneities can cause spikes in the growth curve. Thus, controlling and accounting for anomalies is especially important when using co-amplification data to quantitate the concentration or amount of a target nucleic acid.

In steps 124 and 134, a growth curve value such as an "elbow value" is determined for the target and standard data, respectively. A growth curve value is typically based upon the target or signal data and is typically specified with respect to a growth curve represented by those data. For example, a growth curve value can be a measure of the cycle number at which the signal represented by the growth curve is approximately equal to a predetermined signal value. Preferably, such a growth curve value has precision greater than an integer cycle number, for example, a fractional cycle number. The predetermined signal value is referred to here as an "arbitrary" signal value or "ASV," because many values are possible and may be similarly suitable.

The ASV is preferably defined so that each of the growth curves being analyzed crosses the ASV in its elbow region, in which case the growth curve value is called an elbow value. As discussed previously, a PCR growth curve is typically and generally exponential in form, at least during the initial stages of a PCR, and so tends to have an initial region characterized by a very gradual increase and a latter region where the concentration or amount of product increases rapidly. The elbow region is at the transition from the initial region to the latter region, where the concentration or amount of product is just beginning to increase rapidly. The mathematics of the PCR is typically simpler at the elbow region than at other regions of the curve, such as later in the PCR when competitive effects slow the rate of amplification or growth. In addition, growth is most precisely monitored by using measurements in the elbow region, when changes in the concentration of product from one cycle to the next are largest.

To determine the elbow value for a given growth curve, the growth curve is first normalized according to a defined baseline so that the signal data begin, for example, at a value of one or zero. Data points on the growth curve that are close to the arbitrary signal value are then identified, and the elbow value is determined by interpolating between the cycle numbers associated with those data points.

Figure 3:
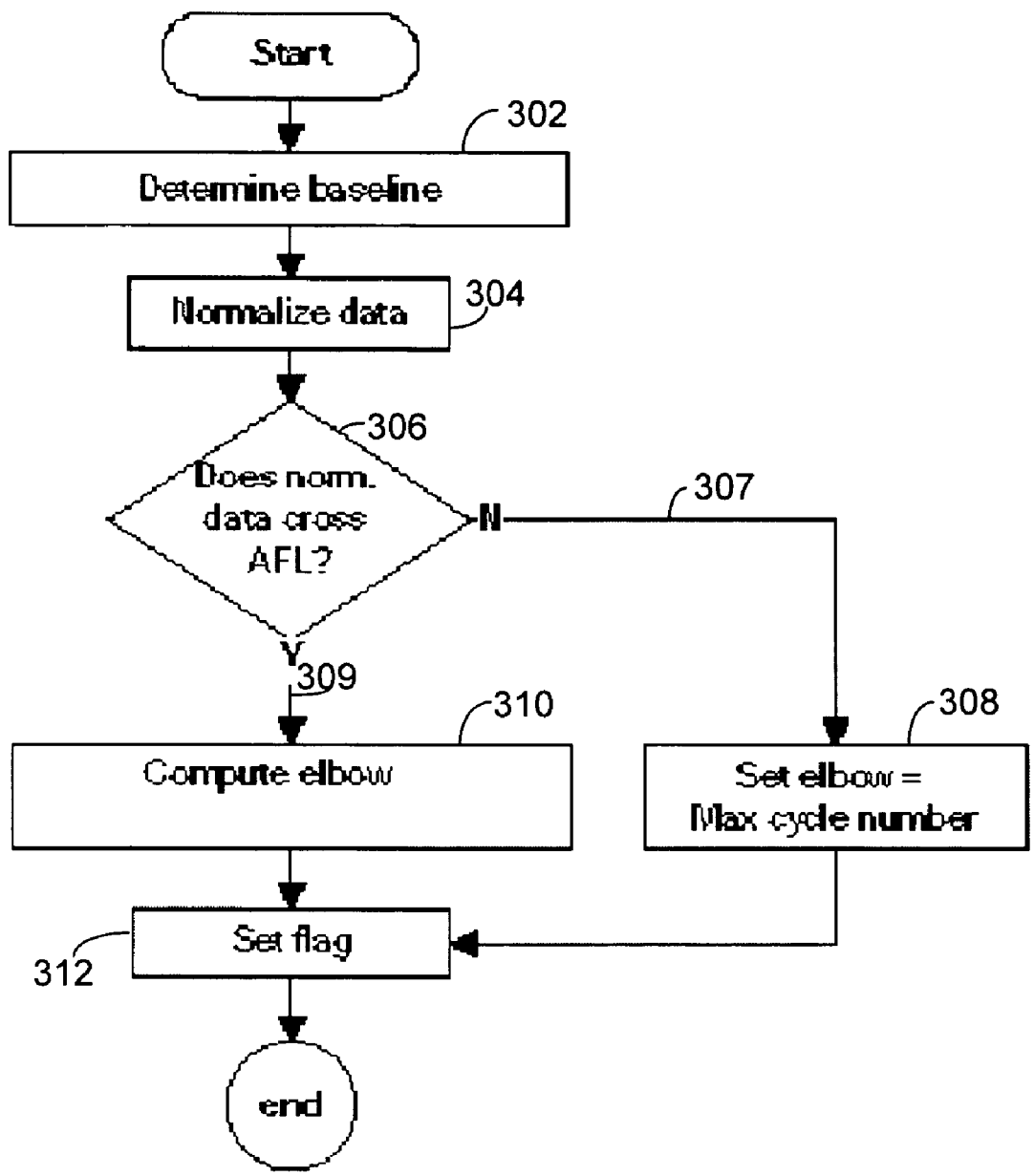
FIG. 3 illustrates a method for calculating an elbow value according to one aspect of the invention.

More precisely and as shown in FIG. 3, determining the elbow value begins by determining the baseline of the growth curve (step 302). A fixed range of cycles can be used, for example, from $BL_{start}$ to $BL_{stop}$. Alternatively, the range of cycles to be used can be chosen based upon the data, as explained in more detail below.

Figure 4A:
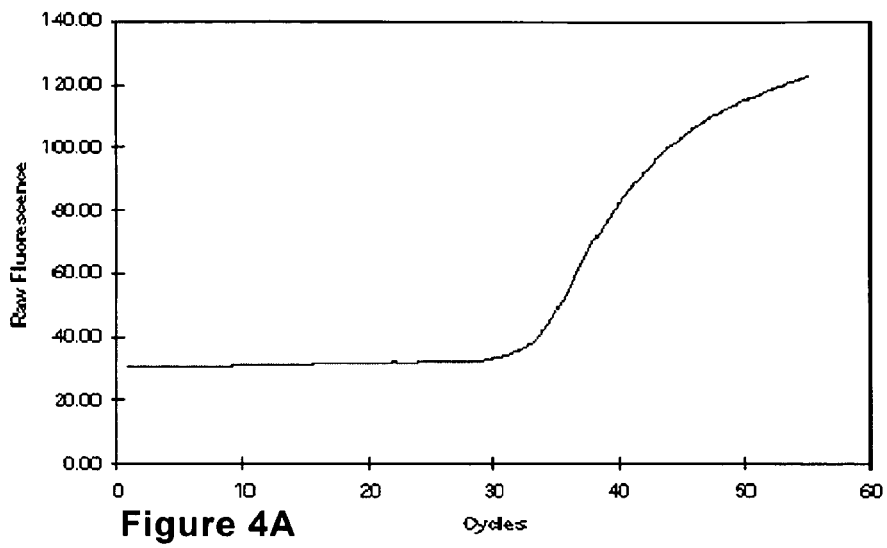
FIGS. 4A-C show a growth curve represented by raw signal data, the data after normalization with a method that assumes no slope, and the data after normalization with a method that takes into account baseline slope, respectively.

In a simple and standard model, the slope of the baseline is assumed to be zero, which may or may not be accurate. The intercept ($BL_{int}$) of the baseline is the signal value where the growth curve crosses the y-axis. It can be calculated as the average ($BL_{avg}$) of the signals for each cycle within the selected range of cycles, for example, from $BL_{start}$ to $BL_{stop}$ inclusive. An example of raw signal data is shown in FIG. 4A. The growth curve crosses the y-axis at a signal value of about 30. The baseline is defined as:

$$S = BL_{avg} \tag{2}$$

Figure 4B:
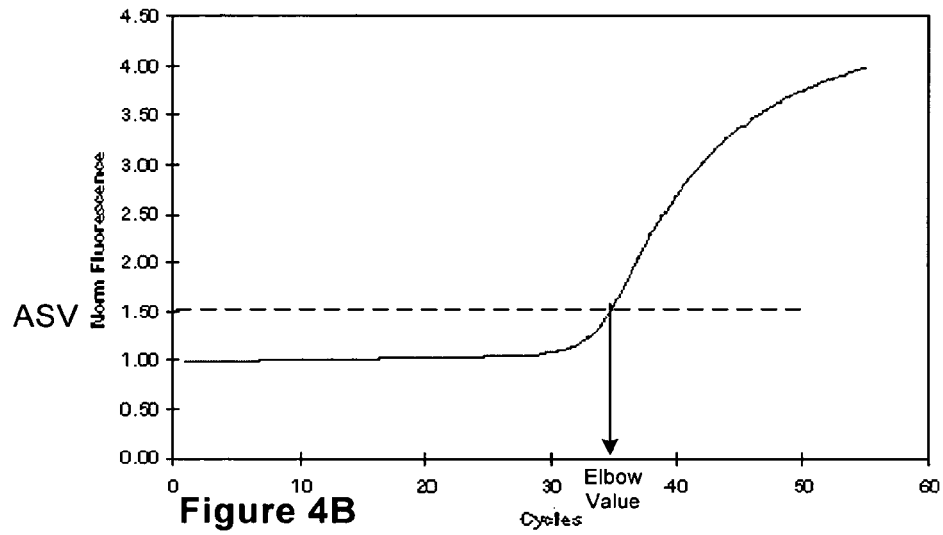

The signal data are normalized using the calculated baseline (step 304). For example, the raw signal data can be normalized so that the growth curve crosses the y-axis at about 1.0, as shown in FIG. 4B, according to the following equation:

$$S_{norm} = S_{raw}/BL_{avg} \tag{3}$$

In a more realistic model, an intercept and a slope ($BL_{slope}$) of the baseline can be estimated from signal data, for example, using linear regression. This new model can account for linear drift in the baseline. In this model, for a signal, S, and cycle number, C, the baseline is defined in step 302 as:

$$S = (BL_{slope} * n) + BL_{int} \tag{4}$$

Figure 4C:
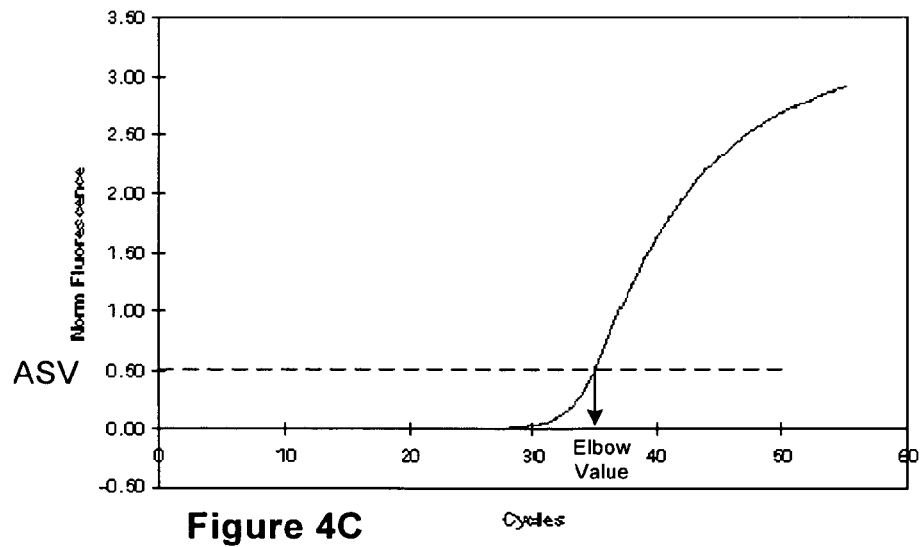

In normalization step 304, and as shown in FIG. 4C, the signal data can then be normalized as:

$$S_{norm} = [S_{raw} - (BL_{slope} * n)]/BL_{int} - 1 \tag{5}$$

The baseline intercept for data normalized according to the model of equations (4) and (5) has a baseline intercept of 0.00, whereas the baseline intercept for data normalized according to the simpler model of equations (2) and (3) is 1.00. Also, both models can be used for growth curves containing baseline dips or data spikes, data that is not equally spaced, and data that includes baseline steps, but the resulting parameter values may be adversely affected by such spurious data. For example, the presence of upward spikes may result in a larger than appropriate intercept value.

After the data is normalized according to the calculated baseline, the data is checked to determine whether the normalized growth curve crosses an arbitrary signal value, ASV ($n_{ASV}$) (step 306). An Offset Cycle number can be used to indicate the cycle number at which to begin checking for data near the ASV. In this case, the elbow value must be greater than the Offset cycle number to be valid. If there is no such data (the "No" branch, 307), a value indicative of a negative sample can be returned, or the elbow value can be set to equal the maximum cycle number (step 308). If the growth curve does cross the ASV (the "Yes" branch, 309), the elbow value is calculated from the signal data (step 310).

The elbow value can be calculated by interpolating between signal values close to the ASV to find the cycle number where the signal value is approximately equal to the ASV. For example, for the cycle number, $n_{hi}$, of a signal value $Y_{hi}$ close to and above the ASV, $n_{ASV}$, and the cycle number, $n_{lo}$, of a signal value $Y_{lo}$, close to and below the ASV, the elbow value can be calculated by a two-point linear interpolation as:

$$n_{ASV} = n_{lo} + [(Y_{ASV} - Y_{lo})/(Y_{hi} - Y_{lo})] * (n_{hi} - n_{lo}) \quad (6)$$

Alternatively, the elbow value can be calculated by a two-point logarithmic interpolation as:

$$n_{ASV} = n_{lo} + \frac{\log[(Y_{ASV} - 1)/(Y_{lo} - 1)]}{\log[(Y_{hi} - 1)/(Y_{lo} - 1)]} * (n_{hi} - n_{lo}) \quad (7)$$

After computing the elbow value, a flag can be set to indicate whether the value reflects a calculation, in which case quantitation is possible, or a value indicative of a negative sample, in which case quantitation is inappropriate (step 312).

Figure 5A:
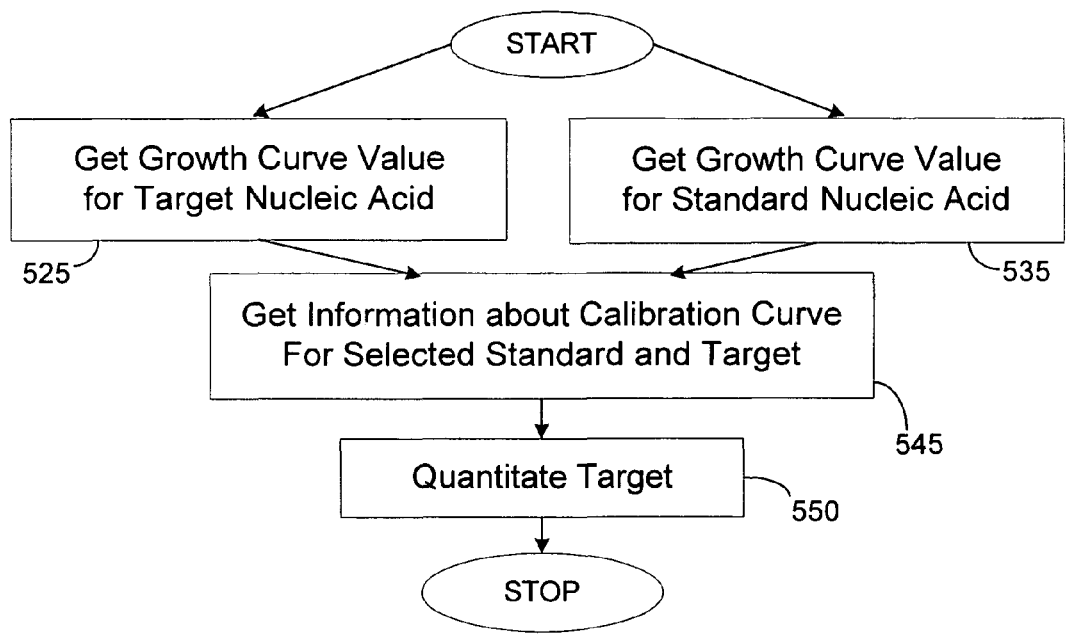
FIG. 5A is a flow diagram illustrating a method for quantitation of a target nucleic acid using a growth curve value for the target nucleic acid and a growth curve value for a standard nucleic acid according to one aspect of the invention.

As shown in FIG. 5A, a growth curve value for the target nucleic acid and a growth curve value for a standard nucleic acid can be used to quantitate the amount of target nucleic acid. In steps 525, 535 the method gets a growth curve value for the target nucleic acid and a growth curve value for the standard, respectively. For example, the method gets an elbow value for the target and an elbow value for the standard, as described for steps 124 and 134, respectively. In step 545, the method gets information that defines a calibration curve or equation for the selected standard and target. The calibration curve can, for example, express the quantity of the target nucleic acid as a function of the concentration of the standard nucleic acid using information from the growth curves of known concentrations of the target nucleic acid and the standard nucleic acid, as explained in more detail below. Finally, in step 550, the calibration equation is used to determine the amount of target nucleic acid in the sample.

Figure 5B:
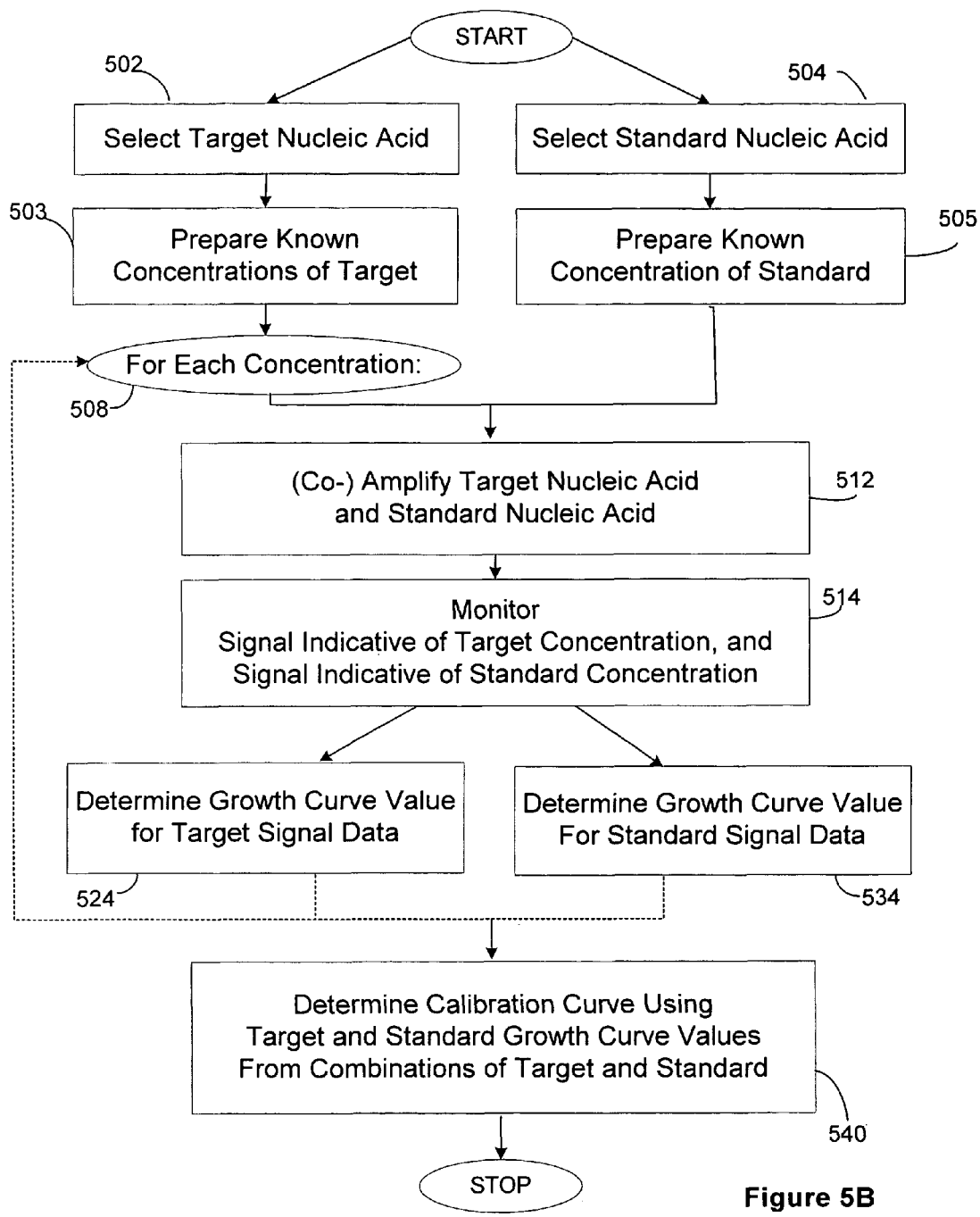
FIG. 5B is a flow diagram illustrating a method for determining a calibration curve for a target nucleic acid and a standard nucleic acid using growth curve values according to one aspect of the invention.

A method for determining a calibration curve for a target nucleic acid and a standard nucleic acid using growth curve values is shown in FIG. 5B. A calibration curve can be defined using information such as growth curve values for a titration of the target and standard. For example, a calibration curve is defined using information from multiple samples of the target that vary in concentration, each of which is, for example, co-amplified with a known quantity of the standard.

The method of calibration for a target and a standard nucleic acid begins (steps 502, 504) by identifying a target nucleic acid and a standard nucleic acid. The target nucleic acid may be of special interest, for example, in the diagnosis of disease. For example, the target may be human immunodeficiency virus (HIV), hepatitis A virus (HAV), or hepatitis B virus (HBV). The standard nucleic acid is typically selected so that it can be amplified using the same pair of primers that are used to amplify the target nucleic acid, as discussed previously. The target and standard nucleic acids that are used to determine a calibration curve are the same as the target and standard nucleic acids that are used to quantify the target, as discussed previously.

The standard can be prepared to have a known initial concentration (step 505), while the target is typically prepared to have various known initial concentrations (step 503). For example, there can be multiple samples of the standard having the same concentration or quantity of standard, and there can be a dilution series of the target having samples of increasing or decreasing concentration or quantity. For each concentration of the target (step 508), the target and a sample of the standard nucleic acid are then amplified (step 512), each amplification is monitored (step 514), a growth curve value is determined for the target (step 524), and a growth curve value is determined for the standard (step 534), for example, as described previously. More generally, one or more concentrations of target can be combined with one or more concentrations of standard and, for each combination, the target and standard are amplified (step 512), monitored (step 514), a growth curve value is determined for the target (step 524), and a growth curve value is determined for the standard (step 534), for example, as described previously.

In step 540, the growth curve values determined for the combinations of known concentrations or quantities of standard and target are used to determine a calibration curve. For example, and as described in more detail below, a measure of the relative concentration or quantity of target and standard can be related to the difference in growth curve values with a second-order polynomial expression (quadratic equation).

The calibration can rely on an underlying model of exponential growth. As described previously, amplification of a nucleic acid by PCR is generally an exponential process during its early stages. The extent of amplification (C) after some number of cycles, $n_N$, can be given, for example, by the equation:

$$C = C_0(1+\epsilon)^{n_N} \quad (8)$$

where $C_0$ is the initial amount of material and $\epsilon$ is the efficiency of amplification. The concentration of standard, Q, and target, T, after some number of cycles, $n_Q$ and $n_T$, respectively, can therefore be defined as:

$$Q = Q_0(1+\epsilon_Q)^{n_Q} \quad (9)$$

$$T = T_0(1+\epsilon_T)^{n_T} \quad (10)$$

As shown below, using equations (9) and (10) and assuming $\epsilon_Q = \epsilon_T$ we can define a proportionality measurement or calibration equation for the initial concentrations of target and standard:

$$\log\frac{T_0}{Q_0} = \log f + (n_Q - n_T) \cdot \log(1 + \varepsilon) \quad (11)$$

That is, if we begin with $$\frac{T}{Q} = f, \text{ where } f = \text{constant of proportionality} \quad (12)$$

we can rewrite f using equations (9) and (10) as $$\frac{T_0 \cdot (1 + \varepsilon_T)^{n_T}}{Q_0 \cdot (1 + \varepsilon_T)^{n_Q}} = f. \quad (13)$$

Then, if we assume that $\varepsilon_Q = \varepsilon_T$ (a reasonable assumption when the same primer is used to amplify the target and standard), we have $$\frac{T_0}{Q_0} = f \cdot (1 + \varepsilon_Q)^{n_Q - n_T}, \quad (14)$$

which can be rewritten as $$\log\frac{T_0}{Q_0} = \log f + (n_Q - n_T) \cdot \log(1 + \varepsilon). \quad (11)$$

Equation (11) is of the form for a line, y=b+xm. Accordingly, the log of the ratio of the initial concentrations of target and standard, log $(T_0/Q_0)$, should be related to the difference in cycle numbers, $(n_Q-n_T)$; that is, it should be a function of the horizontal displacement of the target and standard growth curves. By this equation, a calibration plot of the growth curve data for the various combinations of concentrations of target and nucleic acid, in particular, a plot of log $(T_o/Q_o)$ against $(n_Q-n_T)$, should deliver a straight line.

Figure 6:
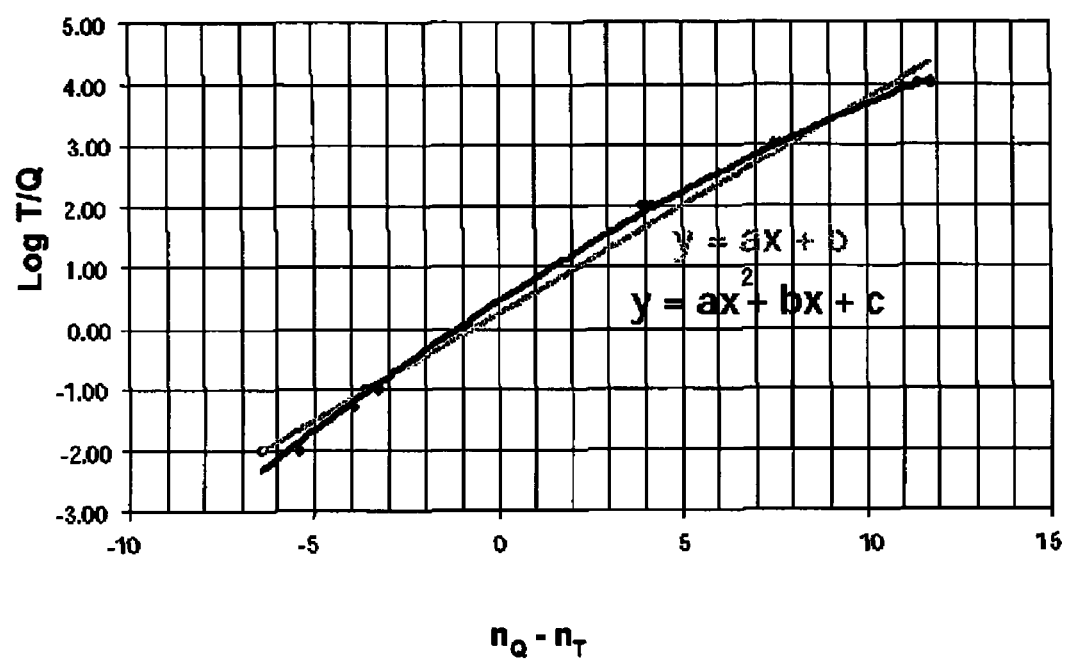
FIG. 6 shows two calibration curves for growth curve data from co-amplifications of two nucleic acids using various ratios of initial concentration.

However, as illustrated in FIG. 6, plotting actual concentrations of log $(T_o/Q_o)$ against measurements of $(n_Q-n_T)$ typically does not reveal a straight line. Rather, a plot of actual concentrations of target and standard against growth curve values such as elbow values determined from their co-amplification reveals a curve.

Without intending to be bound by theory, it is believed that the curved shape of the calibration plot is due in part to competitive effects in the co-amplification of the target and standard nucleic acids; that is, the two PCRs interfere with one another, such that their amplifications do not proceed as predicted or as they would in isolation from each other. Such competitive effects can include substrate saturation of enzyme, product inhibition of enzyme, incomplete product strand separation, and product strand re-annealing. Also, chemicals that are present in the PCR may act as inhibitors to amplification, and may have differential effects on the target and standard, resulting in non-linearities. Moreover, the data are generated from signal data, rather than actual concentrations, and signal data may not be linearly related to actual concentrations. Such indirection in the measurement of concentration can also introduce non-linearities to the calibration plot.

Accordingly, the data for the calibration plot are better approximated by a higher order calibration equation, for example, an equation of the form for a parabola, $y=ax^2+bx+c$ such as:

$$\log(T_o/Q_o) = a(n_Q-n_T)^2 + b(n_Q-n_T) + c \quad (15)$$

Calibration equation (15) can be rewritten as an expression for the initial concentration of the target nucleic acid, given the initial concentration of the standard nucleic acid, a growth curve value $n_T$ for the target, a growth curve value $n_Q$ for the standard, and any calibration coefficients. In particular, solving for the initial quantity of the target nucleic acid, $T_0$, gives the quantitation equation:

$$T_o = Q_o 10^{a(n_Q-n_T)^2+b(n_Q-n_T)+c} \quad (16)$$

The second order form of this quantitation equation appropriately and accurately represents the observed relationships between the target and standard growth curves, and can extend the dynamic range of the assay three to four orders of magnitude above what is currently achievable.

To obtain the most reliable calibration of specific nucleic acids using the described techniques, the range of initial concentrations for the standard and target nucleic acids, as well as the number of amplification cycles, should be such that the reactions remain within the exponential phase of growth. Initial concentrations are typically determined by Poisson analyses or analyses using WHO standards. In addition, to obtain the most reliable quantitative evaluation of a target nucleic acid, the range of initial concentrations of the target that are used to define the calibration equation should encompass the actual concentration of the target in the sample being quantitated.

The methods described above can be implemented and automated using a series of algorithm modules. For example, a computer program application implementing the techniques described herein can include modules that check and correct anomalies in growth curves (steps 122, 132), calculate the elbow value (steps 124, 134), and perform quantitation (step 550). Software can be created to perform these techniques and deliver either a valid result (target not detected, concentration below dynamic range, concentration in range, or concentration above dynamic range) or an invalid result (cannot perform quantitation).

Figure 7A:
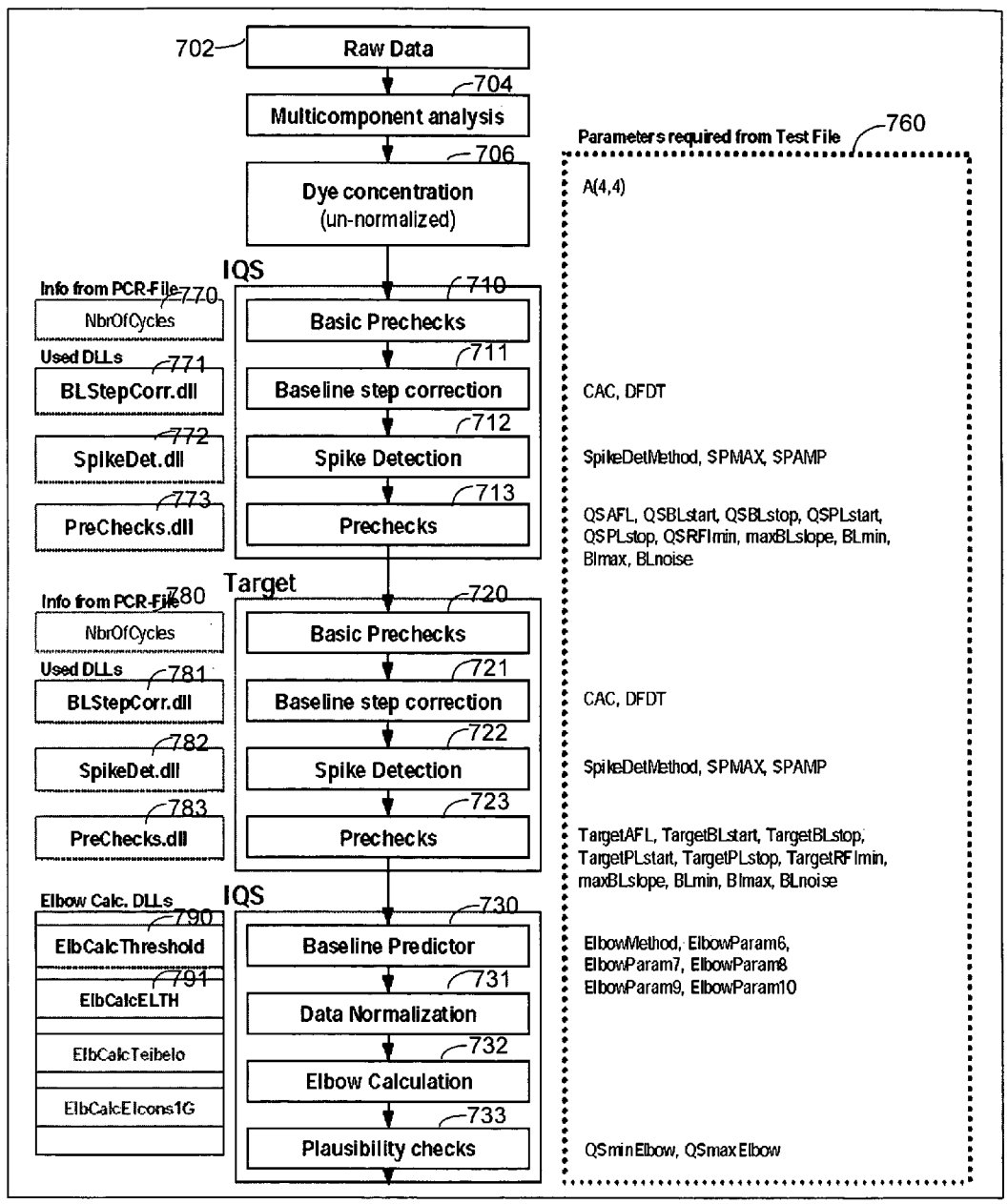
FIGS. 7A-B show an example method for quantitation of a target nucleic acid using growth curves according to one aspect of the invention.
Figure 7B:
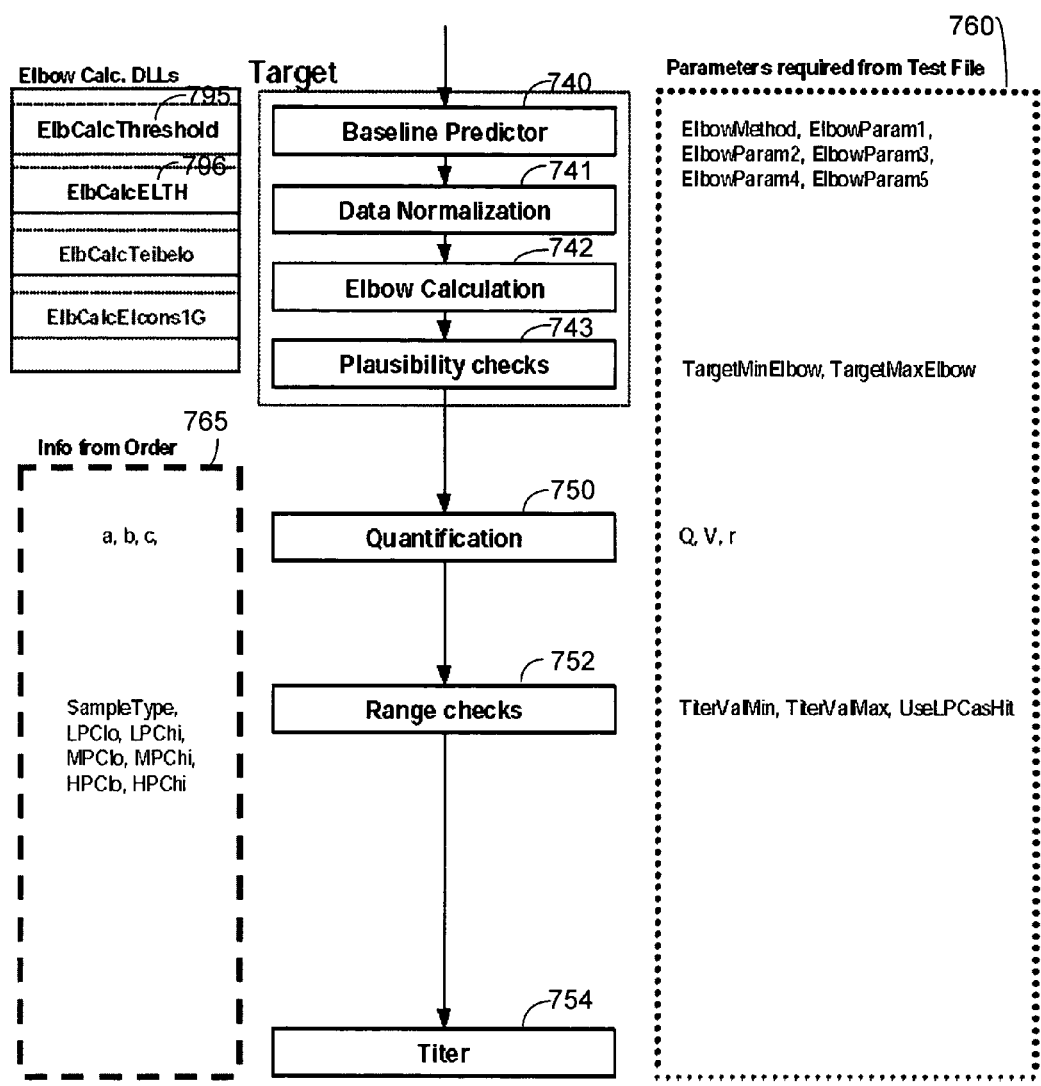

Modules that check and correct anomalies in growth curves (e.g. steps 122, 132) can include a precheck module operable to perform a series of prechecks, which identify noise and drift in an appropriate range of the baseline; a spike detector module, which identifies and corrects or removes spikes; and a baseline step correction module, which corrects shifts in the baseline. These modules, as well as additional plausibility and range checks, can be integrated with the measurement of elbow values (e.g. steps 124, 134) and quantitation (e.g. step 550) of the target into a quantitation method 700, as shown in FIGS. 7A-B.

The quantitation method 700 uses the raw signal data 702 for the target and standard nucleic acids. The raw signal data 702 for each nucleic acid can include, for example and as discussed previously, two filter measurements of fluorescence. If there is a pair of filter measurements for each nucleic acid, each pair of filter measurements is analyzed (step 704) with a multi-component method (described in more detail below) to yield a summary signal value of signal or "dye concentration" (706). All the summary signal values for each nucleic acid are then used in further analyses that call for signal data.

In the ensuing steps (710-743), each set of signal data 702 is processed in the same manner. The signal data for the standard nucleic acid are preferably processed before the signal data for the target nucleic acid are processed. Thus, steps 710-713 are performed using the standard signal data, and analogous steps 720-723 are performed using the target signal data. Similarly, steps 730-733 are performed beginning with the standard signal data from step 713, and analogous steps 740-743 are performed beginning with the target signal data from step 723. Each pair of analogous steps, e.g. step 710 for the standard and step 720 for the target, will be discussed together below.

The checking and correcting (steps 122, 132, FIG. 1) of the signal data (for the standard and for the target, respectively) begins with basic prechecks (steps 710, 720). For example, the data are checked to confirm that there are signal data values for an appropriate number of amplification cycles. In the next two steps, each of which are explained in more detail below, each set of signal data is checked for baseline shifts (steps 711, 721) and signal spikes (steps 712, 722). If baseline shifts are encountered, they are characterized and corrected. If spikes exist, they may or may not be corrected or removed. After the data are corrected for baseline shifts and possibly for spikes, a series of prechecks are conducted (steps 713, 723). The prechecks assess whether an elbow value should be determined. For example, the prechecks assess whether the data fall within certain limits of plausibility.

If the data are found to be suitable in steps 713, 723, a growth curve value such as an elbow value is determined (steps 730-733, 740-743), for example as described previously. In this process, a baseline is defined (steps 730, 740), the signal data are normalized (steps 731, 741), and the elbow value is calculated, for example, by interpolation between normalized data points (steps 732, 742). The final step in this process is a check for the plausibility of the elbow values (steps 733, 743), for example, by comparing the values to defined limits of plausibility.

If the elbow values are found to be plausible, they are used to quantitate the target (step 750), for example, as described previously. The value for the quantity of target is then checked (step 752) to confirm its plausibility, for example, by comparing it to plausibility limits, and to determine how the result should be reported. The plausibility limits can be defined, for example, by the range of concentrations of target used to determine the calibration equation for the quantitation. In one implementation, this range check can produce one of five possible results, depending upon a particular range of acceptable values Min to Max:

| | |
|---|---|
| 1. Invalid | a failure or abort in the quantitation method. |
| 2. >Max | elbow value determined, but quantity greater than Max. |
| 3. Quantity | elbow value determined, and quantity within range. |
| 4. <Min | elbow value determined, but quantity less than Min. |
| 5. Not Detected | no elbow value found. |

Multiple ranges can be set. For example, an acceptance range can be set and then, within the acceptance range, precision ranges such as low, medium, and high can be set, where the high precision range is the narrowest range. A low positive control may serve as a hit rate control for some assays, such that a quantity below this limit may be valid if it is clearly differentiated from the outcome for "Target not detected."

Finally, the value for the quantity of target—the titer—is determined (step 754). For example, one of the five possible results can be reported for each of the defined ranges.

At each step in method 700, flags can be set to indicate the outcome of checks or analyses. For example, flags can be generated to indicate that the data exhibited baseline shifts or spikes, to explain where the data lie with respect to certain limits, or to keep track of any strange data, math errors, or system failures.

Quantitation method 700 may require that certain parameters 760 be defined. Such parameters can be defined and stored in a test file, and accessed as needed by the method 700. For example, prechecks (steps 713, 723, above) and plausibility checks (steps 733, 743, above) require that the ranges of plausible values be defined, for example, by minimum (min) and maximum (max) values. Determination of the elbow value requires definition of parameters including, for example, definition of the arbitrary signal value (ASV). The test file parameters are typically specific to the assay being used. However, the analogous parameters for the target and standard data may be different, since the nucleic acids and the mechanisms used to detect them (e.g. the fluorescent dyes) may have different behavior.

Quantitation method 700 also may require information pertaining to the PCR of the target and standard nucleic acids. For example, basic prechecks (steps 710, 720, above) may require inputs including the number of cycles 770, 780 that were used in the PCR. Such information can be stored in a PCR data file, and retrieved as needed by the method 700.

Quantitation method 700 typically also requires information pertaining to the specific application or use of the method, for example, for quantitation. To perform quantitation, information about the calibration equation is provided to the quantitation method, for example, as specified in an "order" file 765. Information about the calibration equation can include information defining the target and standard, the form of the calibration equation, and values for the calibration coefficients, as discussed previously. Information about suitable ranges of target can also be provided. For example, a "lo" and "hi" value can be provided to define one or more ranges of acceptability, as discussed previously.

Information pertaining to the specific application or use of the method can be read from a barcode sheet or entered manually.

As shown in FIG. 7A-B, some of the functionality of quantitation method 700 can be implemented in dynamic link libraries (DLL). For example, DLLs can be used to implement a baseline step correction module 771, 781; spike detection module 772, 782; prechecks module 773, 783; and elbow modules 790-796. DLLs can be shared between software implemented in different environments. The use of DLLs allows calculation modules to be validated by an independent piece of software, and allows changes in implementation of the methodology without having to re-build the entire software system. For example, a DLL can be changed and the executable file that calls or references the DLL need not be recompiled.

An exemplary method for performing baseline step correction is as follows.

Figure 8A:
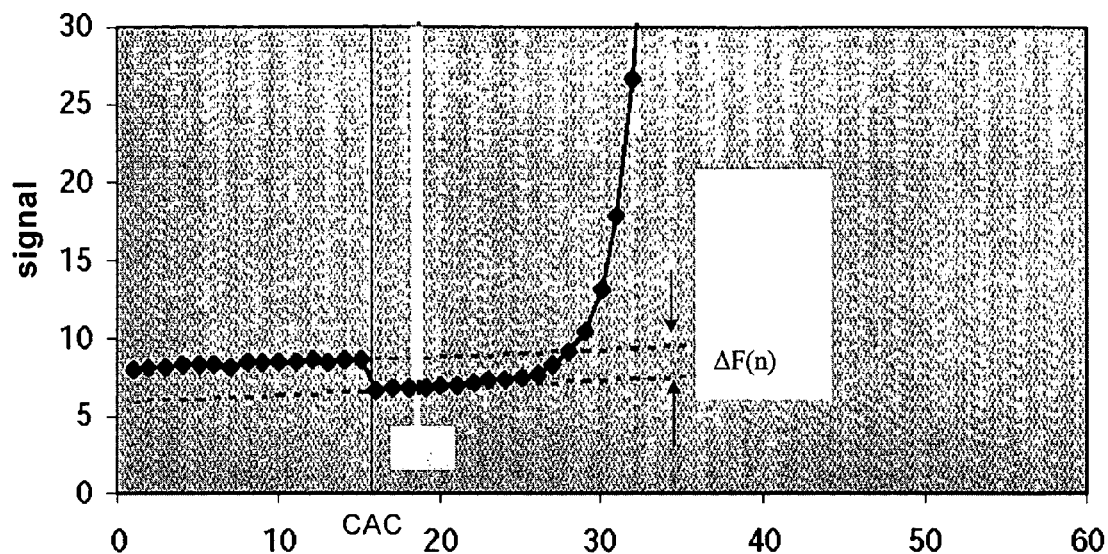
FIGS. 8A-B show growth curves having baseline shifts.
Figure 8B:
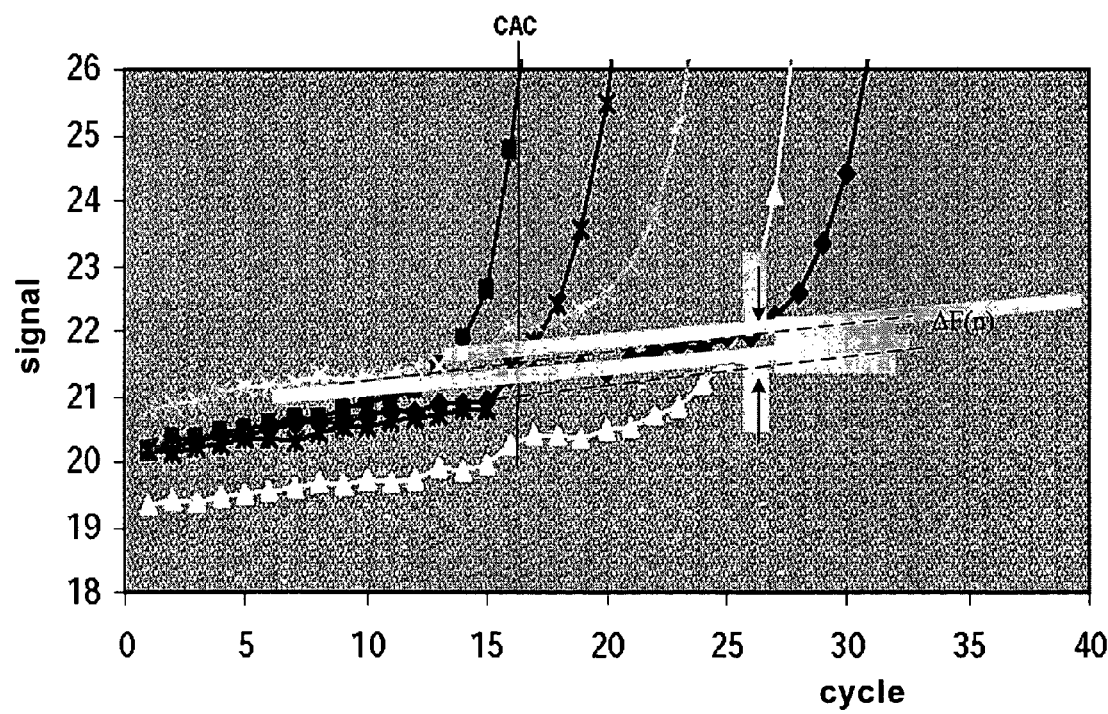

As shown in FIG. 8A-B, a baseline step or shift causes all subsequent points on a growth curve to be shifted down (as shown in FIG. 8A) or up (as shown in FIG. 8B). Baseline steps commonly occur when there is a change in annealing temperature because the fluorescent signals that are measured can vary with temperature. Typically, the intensity of fluorescence is proportional to temperature.

The cycle of an annealing change is designated CAC. In the examples shown in FIG. 8A-B, the annealing temperature is changed at cycle 15 from 60 to 45 degrees C. The direction of the change can depend on the fluorescent dye that is used to detect the nucleic acid. In FIG. 8, the standard growth curves are shown in the first figure, and the target curves are shown in the second figure; the standard and the target nucleic acids are detected using different fluorescent dyes.

The amount of the upward or downward shift in the signals making up the growth curve is designated as the baseline shift, $\Delta F(n)$. $\Delta F(n)$ is defined as:

$$\Delta F(n) = Y_{CAC+1} - Y_{CAC} \qquad (17)$$

where $Y_{CAC+1}$ is the signal value at the cycle after the change in annealing temperature and $Y_{CAC}$ is the signal value at the cycle where the change in annealing temperature occurs (i.e. the first cycle at the new temperature).

The baseline step is most noticeable when it occurs in the baseline of the growth curve (as shown in FIGS. 8A, 8B). The baseline step may be imperceptible if it occurs during rapid amplification (as shown for the leftmost curves in FIG. 8B), because the change due to amplification is much greater than the change due to temperature. Signal changes due to changes in the annealing temperature can be distinguished from changes due to amplification by setting a threshold, DFDT, above which changes are attributed solely to amplification.

Figure 9:
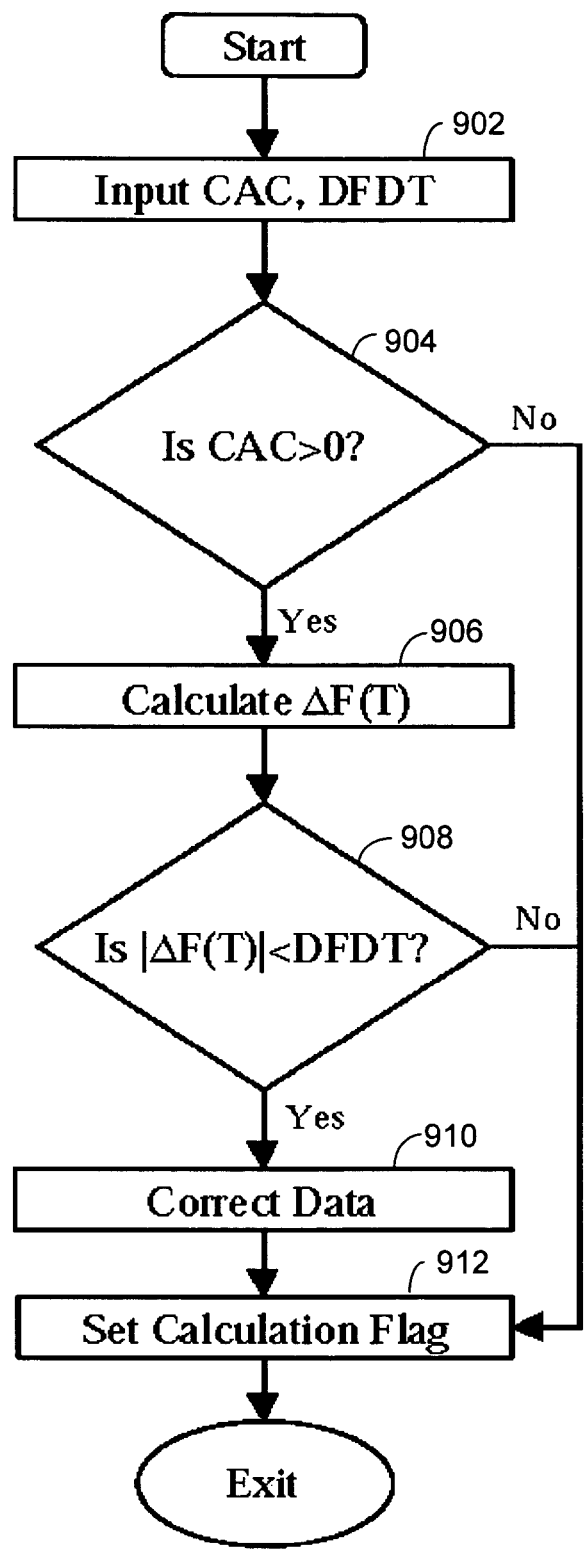
FIG. 9 illustrates a method for identifying baseline shift according to one aspect of the invention.

FIG. 9 shows the steps for assessing a baseline shift. The CAC and a threshold shift value, DFDT, are input (step 902). The CAC is compared to zero (step 904). If the CAC is greater than zero (the "Yes" branch of step 904), the degree and direction of baseline shift, $\Delta F(n)$, is determined (step 906). The absolute value of $\Delta F(n)$ is compared to the threshold, DFDT (step 908). If the absolute value of $\Delta F(n)$ exceeds the threshold (the YES branch of step 908), the data are corrected (step 910) and a flag can be set to indicate that the baseline shift correction was completed (step 912). If the absolute value of $\Delta F(n)$ does not exceed the threshold (the NO branch of step 910), the data is not corrected and a flag can be set to indicate that the correction was aborted (step 912).

If CAC is not greater than zero (the "No" branch of step 904), the algorithm can be by-passed. In this case, a calculation flag can be set to indicate that no baseline shift correction was performed (step 912).

The data from the first cycle to the cycle of the change in annealing temperature, that is, for i=1 to CAC are corrected according to Equation 15:

$$Y_i^{corrected} = Y_i + \Delta F(n) \qquad (18)$$

Figure 10A:
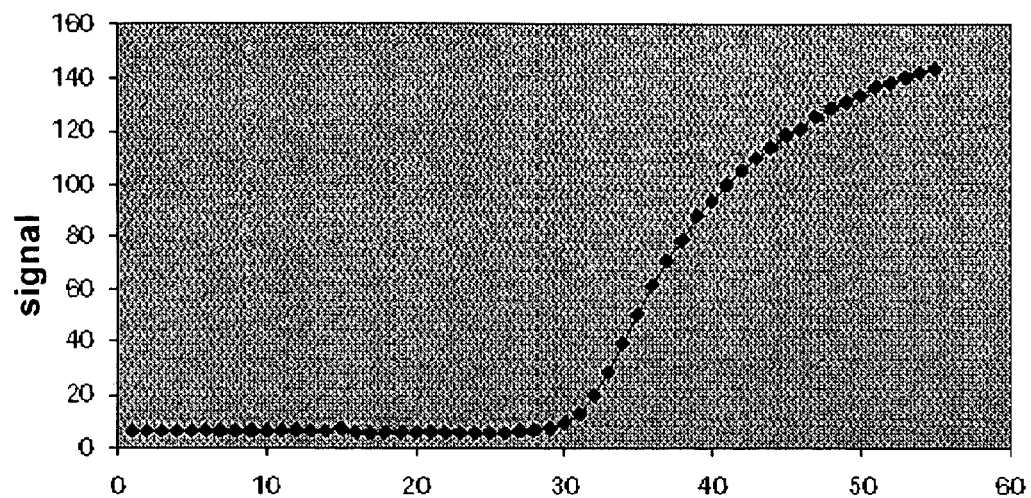
FIGS. 10A-C show a growth curve having a baseline shift, an enlarged view of the baseline shift, and a corrected version of the data, respectively.
Figure 10B:
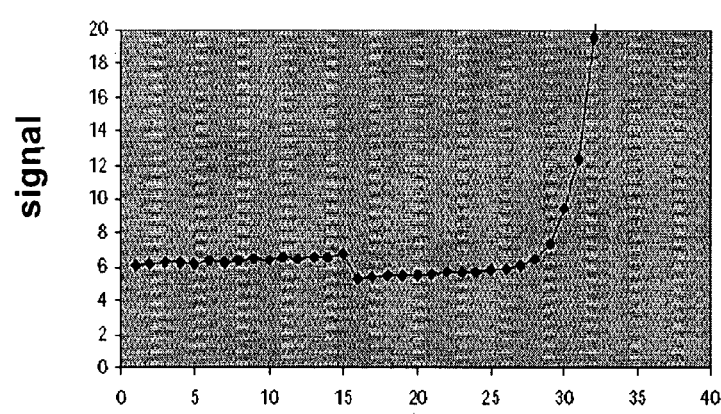
Figure 10C:
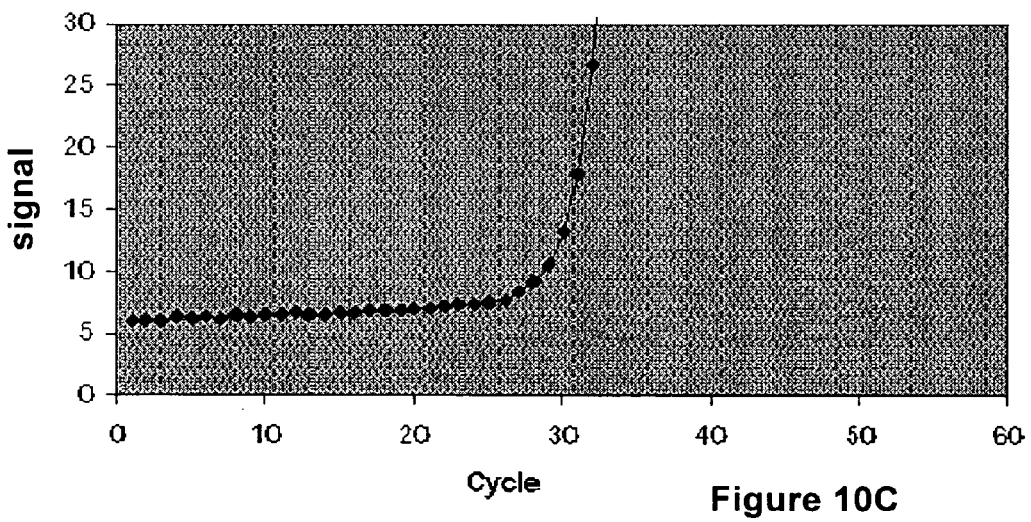

FIGS. 10A-C demonstrate a baseline shift correction. FIG. 10A shows raw data for an amplification in which there was an annealing change at cycle 15. An expanded view in FIG. 10B reveals the baseline shift. In FIG. 10C, a similarly expanded view shows the data corrected as described above.

An exemplary method for performing spike detection is as follows.

Spike detection is dependent on at least two parameters. A SPMAX parameter defines the maximum number of points that can make up a single spike, and is typically between 1 and 4. A SPAMP parameter defines the minimum amplitude that a spike can have. The method obtains the difference between adjacent data points for a block of SPMAX+1 data points to determine the location of possible spike points. If any of the first-order differences are larger than the value SPAMP and have different signs, there may be a spike. A spike is confirmed if there is also a change in sign of the second-order differences.

Figure 11A:
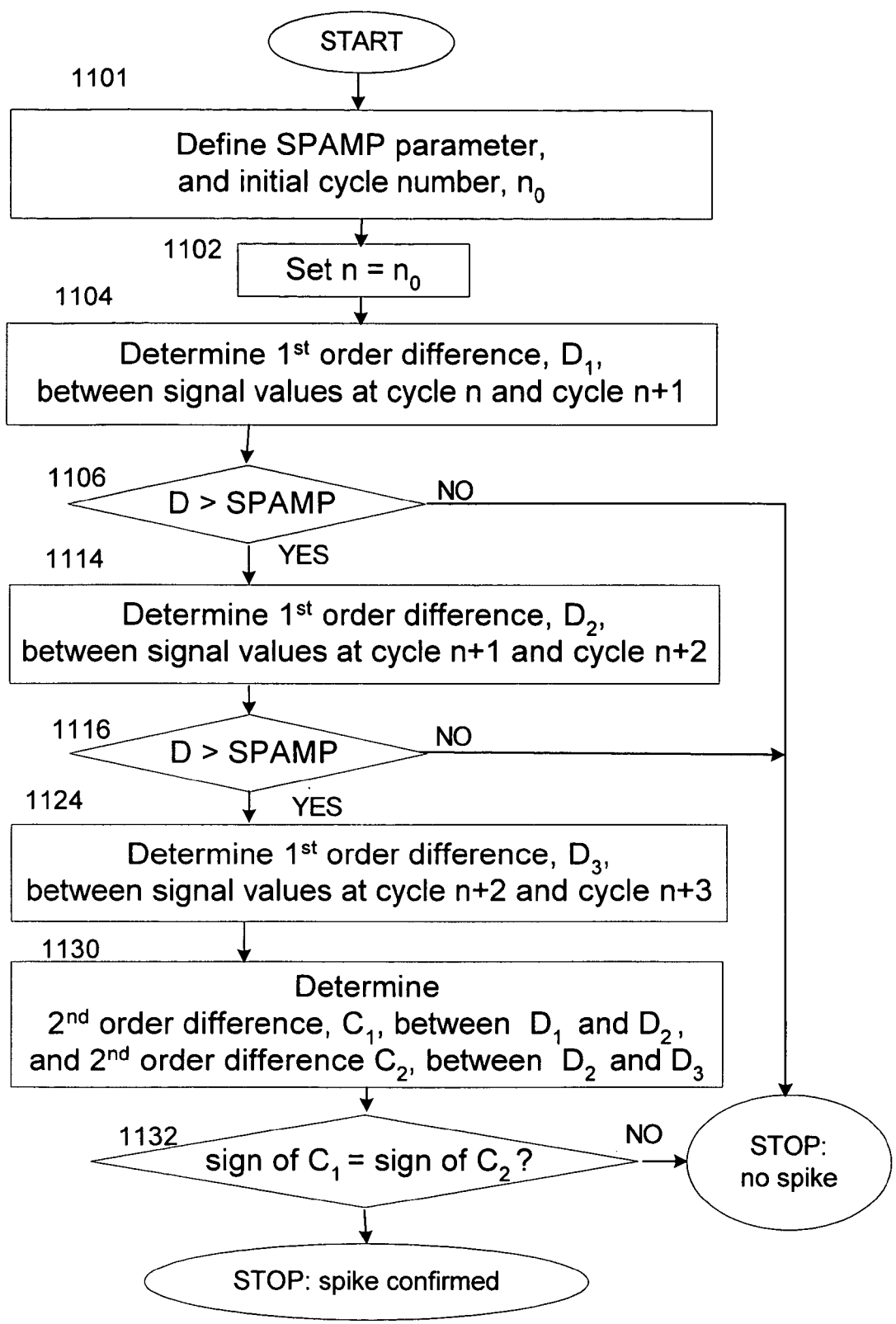
FIGS. 11A-C illustrate a method for identifying spikes.
Figure 11B:
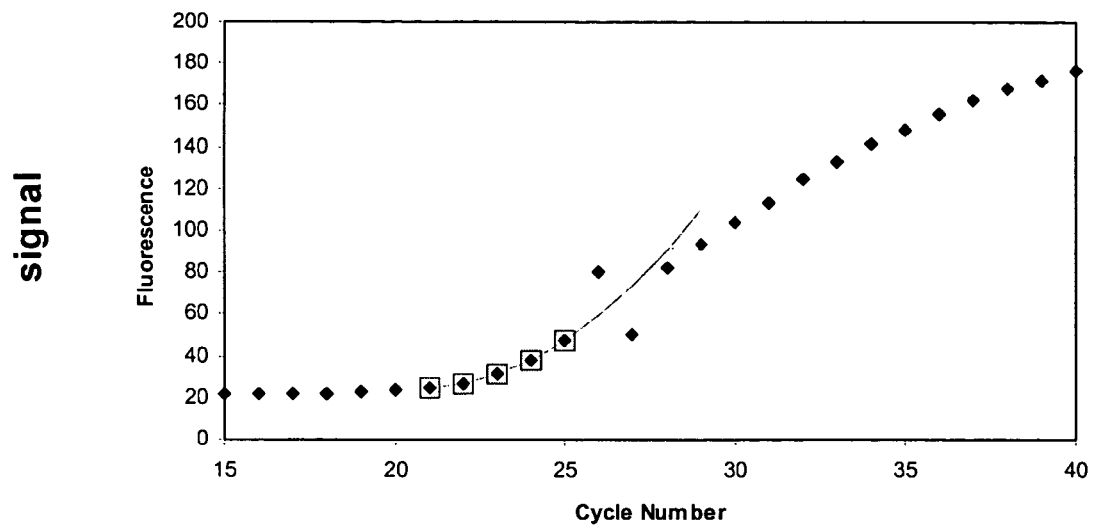
Figure 11C:
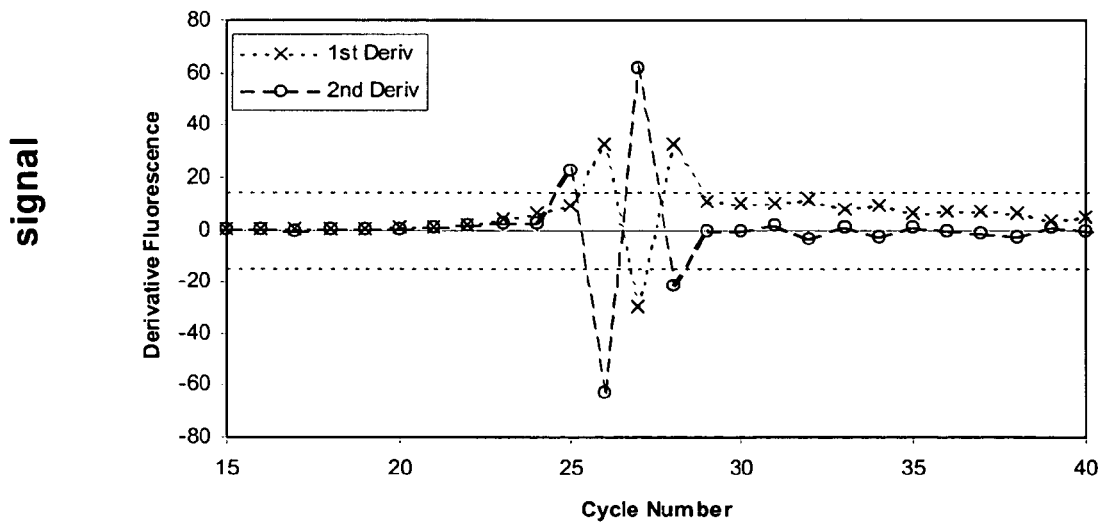

For example and as shown in the flow chart of FIG. 11A, a spike detection method for which SPMAX is 2 begins by defining (step 1101) SPAMP and identifying a cycle number, no, in the PCR amplification. The cycle number n is set no (step 1102). The difference, $D_1$, between the signal value at cycle n and the signal value at cycle n+1 is determined (step 1104). If SPMAX is greater than 2, multiple values can be used to define a first or a second difference. If $D_1$ is not greater than SPAMP (the NO branch of step 1106), the method stops; there is no spike. If $D_1$ is greater than SPAMP (the YES branch of step 1106), then the difference, $D_2$, between the signal value at cycle n+1 and the signal value at cycle n+2 is determined (step 1114). If $D_2$ is not greater than SPAMP (the NO branch of step 1116), then the method stops; there is no spike. But if $D_2$ is greater than SPAMP (the YES branch of step 1116), there is a possible spike. In the case where SPMAX is 2, the difference, $D_3$, between the signal value at cycle n+2 and the signal value at cycle n+3 is determined (step 1124), then the second order difference, $C_1$, is determined as the difference between $D_1$ and $D_2$, and the second order difference $C_2$, is determined as the difference between $D_2$ and $D_3$ (step 1130). If SPMAX is greater than 2, multiple values can be used to define the second order differences. If the signs of the second order differences, $C_1$ and $C_2$ differ (the YES branch of step 1132), then the method stops and a spike is confirmed (step 1136). If the signs of the second order differences do not differ (the NO branch of step 132), the method stops; there is no spike.

A graphical example is shown in FIGS. 1B-C, for SPMAX=2 and SPAMP=15. The method looks for the data points where the first-order difference exceeds the SPAMP and changes in sign. These criteria are satisfied for data points at cycle numbers 25, 26, 27, and 28. However, only data points at cycles numbers 26, 27, and 28 have second-order differences that change sign, so there is a spike among these 3 data points. One of these three points must be a genuine point on the curve, as a spike can only consist of a maximum of two points (SPMAX=2).

To determine which point is genuine, a second-order polynomial is fitted to the 5 data points prior to the spike points and the distance of each spike point from it are determined. Of the 3 spike points in this example, the data point at cycle number 28 is considered to be a genuine point, while the other 2 points are considered to be spikes. Spikes can be corrected by determining another parabola that includes the genuine point, and using it to determine acceptable data values for spike points.

Figure 12A:
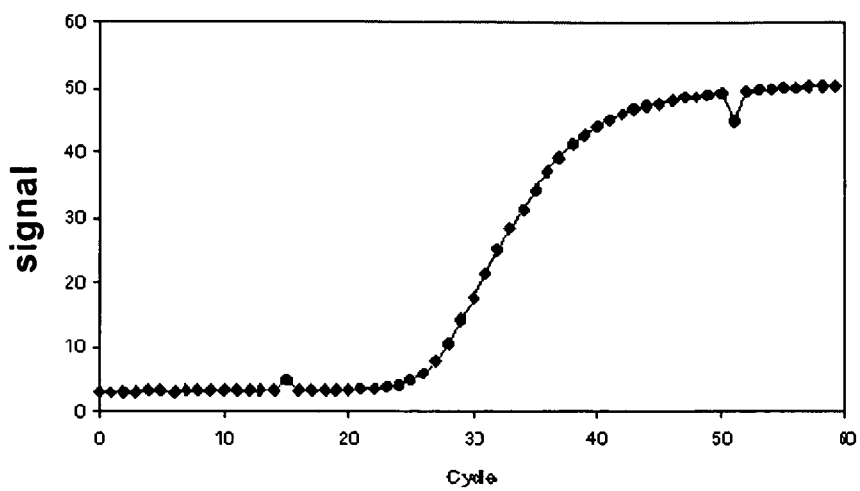
FIGS. 12A-C show a growth curve having two spikes, the growth curve with the spikes corrected, and the growth curve with the spikes removed, respectively.
Figure 12B:
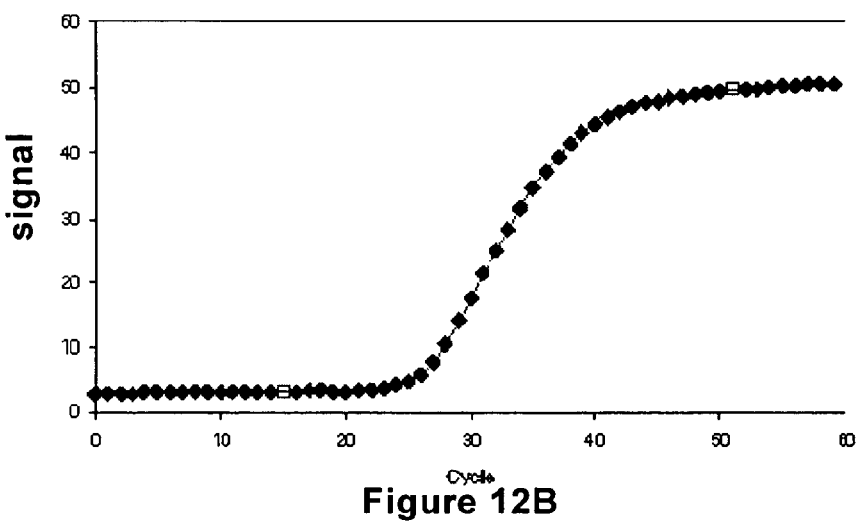
Figure 12C:
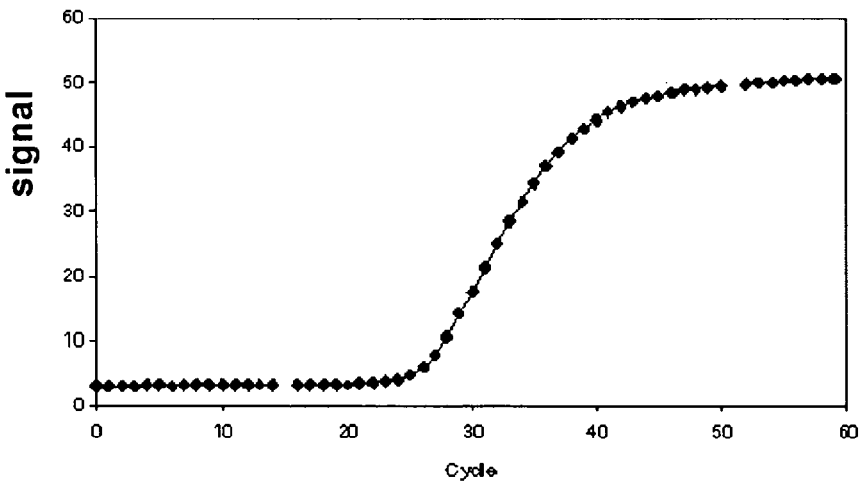

FIG. 12A illustrates a growth curve that has been determined to have two spikes. Spikes can be removed by replacing the spurious data values with no data, as shown in FIG. 12C. Alternatively, spikes can be corrected as shown in FIG. 12B. Signal readings taken at each cycle are assumed to be equally spaced. Ideally, spikes are detected and corrected, so that the spacing of data is preserved. If spikes are detected but not corrected, their presence may introduce inaccuracies to the determination of the elbow value. If spike data are detected and removed, the data set will have fewer than expected and inappropriately spaced data values, which may also introduce inaccuracies to the determination of the elbow value.

Identifying and removing or correcting spikes insures the robustness of the quantitation method. In one implementation, baseline steps are corrected before performing the spike detection method to ensure that data points are equally spaced and continuous.

Figure 13A:
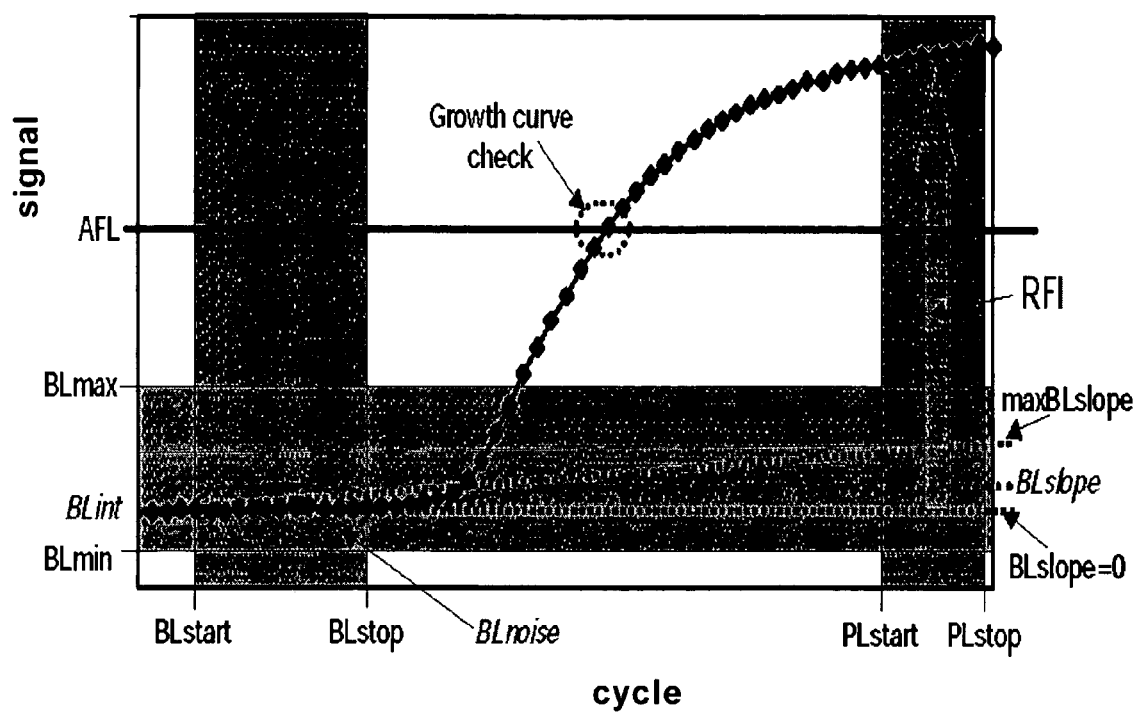
FIGS. 13A-B illustrates several possible prechecks of growth curves.
Figure 13B:
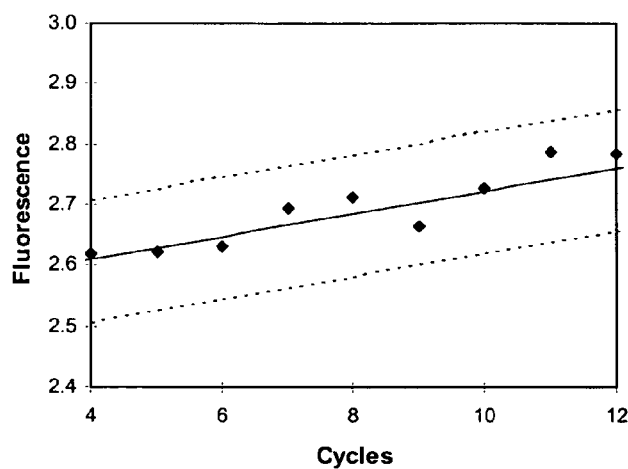

FIG. 13A-B illustrates a number of possible methods to be performed in one implementation of the prechecks discussed above.

The slope of the data points from BLstart to BLstop can be calculated using linear regression. The calculated slope of the baseline can be checked to see that it lies in the range from BLslope=0 to maxBLslope. If the baseline slope is outside this range, quantitation should be aborted.

The noise of the data (BLnoise) can be checked by examining the error of the signal values, y(x), as determined by the linear regression of data from BLstart to BLstop, as shown in FIG. 13A. As shown in more detail in FIG. 13B, the error of this linear regression should be smaller than a threshold level of noise, BLnoise. If the error exceeds this threshold, quantitation should be aborted.

A sample processing error can be detected by examining the intercept for the linear regression of the data points from BLstart to BLstop. The intercept of the baseline should be within a specified range, such as defined by BLmin and BLmax. An intercept that is too high or too low could indicate an empty well, lack of reagent, or lack of sample. In either case, quantitation should be aborted.

The degree of amplification, RFI, can be evaluated by calculating the average of the signals observed late in the PCR, for example, for data points from PLstart to PLstop, and dividing by the average of the signals early in the PCR, for example, between BLstart and BLstop. The RFI should be greater than 1.0. If it is not, quantitation should be aborted.

When spikes are not corrected or removed, an elbow value could be detected by mistake. Therefore, an additional check for spikes can be useful. For example, a check can be made to determine if there is more than one point where normalized fluorescence intensities pass the ASV. Alternatively, a check can be made to determine if the point of intersection of the growth curve and the ASV is close to a known spike by defining a critical range around the ASV or elbow value. If a spike is detected within this critical range, further data processing should be stopped.

One method for performing elbow value calculation was described previously. An alternative method for performing elbow value calculation, which checks for baseline slope, is as follows.

The alternative method dynamically predicts the number of points that fit a set of baseline criteria and corrects for the baseline slope. It uses a 2-point interpolation (either linear or log) to determine the cycle at which the growth curve crosses the AFL, as discussed previously. Interpolations between more than two points can be used. In one implementation, baseline steps, if present, are corrected prior to using this method.

Figure 14:
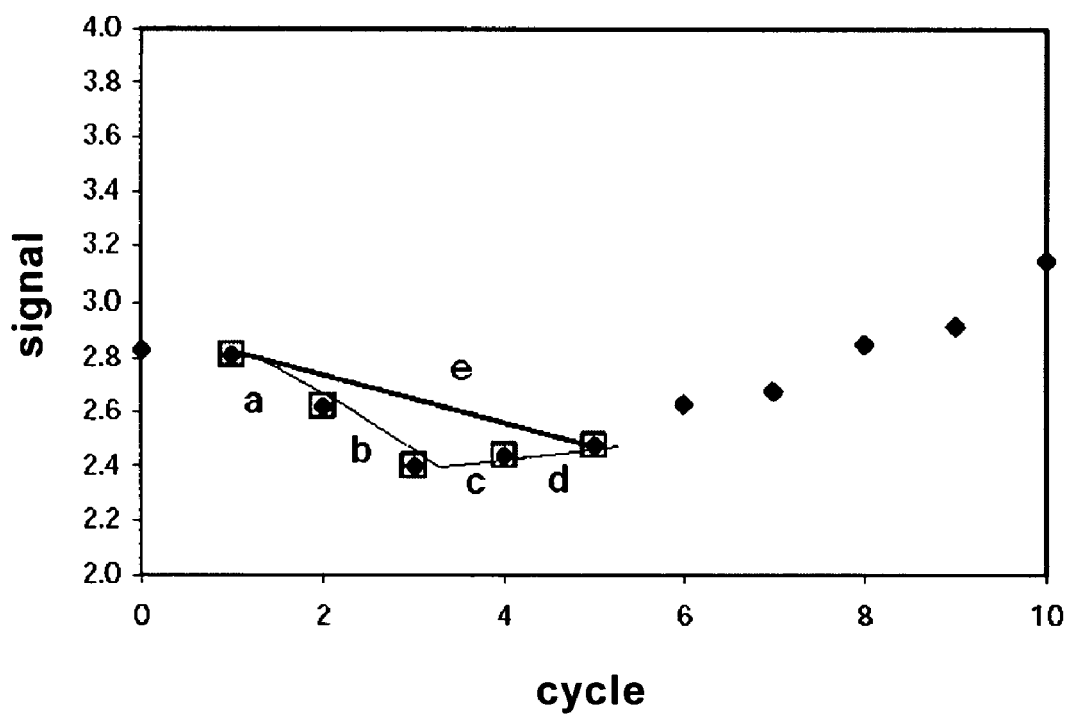
FIG. 14 illustrates a method of identifying baseline slope anomalies while determining an elbow value according to one aspect of the invention.

As shown in FIG. 14, the alternative method for performing elbow value calculation uses a moving 5-point block. The slopes between adjacent points (labeled a thru d) and the slope between the first and fifth points in the block (labeled e) are calculated.

The slopes between adjacent points (expressed at point i) are calculated using the following equation:

$$\Delta Y / \Delta X |_i^{i+1} = (Y_{i+1} - Y_i)/(X_{i+1} - X_i) \quad (19)$$

The slope between the first and fifth points (expressed at point i) is calculated using the following equation:

$$\Delta Y / \Delta X |_i^{i+5} = (Y_{i+5} - Y_i)/(X_{i+5} - X_i) \quad (20)$$

For all 5 points to be considered baseline points, two conditions must be met: (1) the absolute value of each slope, a through d, must be less than a noise input parameter; and (2) the value of slope e must be within a certain range, for example, greater than a threshold value such as −0.1, and less than an error value such as the product of the noise input parameter and a measure of variation in the data. If either condition is not met, the last of the 5 points is not considered part of the baseline.

After calculating slopes a through e, the block is moved to the right, for example, by one cycle, and the calculations are repeated. It is possible that the conditions will be met on one 5-point block but not the next. Thus, this sliding window method produces a set of data that omits bad baseline points (like those encountered during a baseline spike).

Figure 15A:
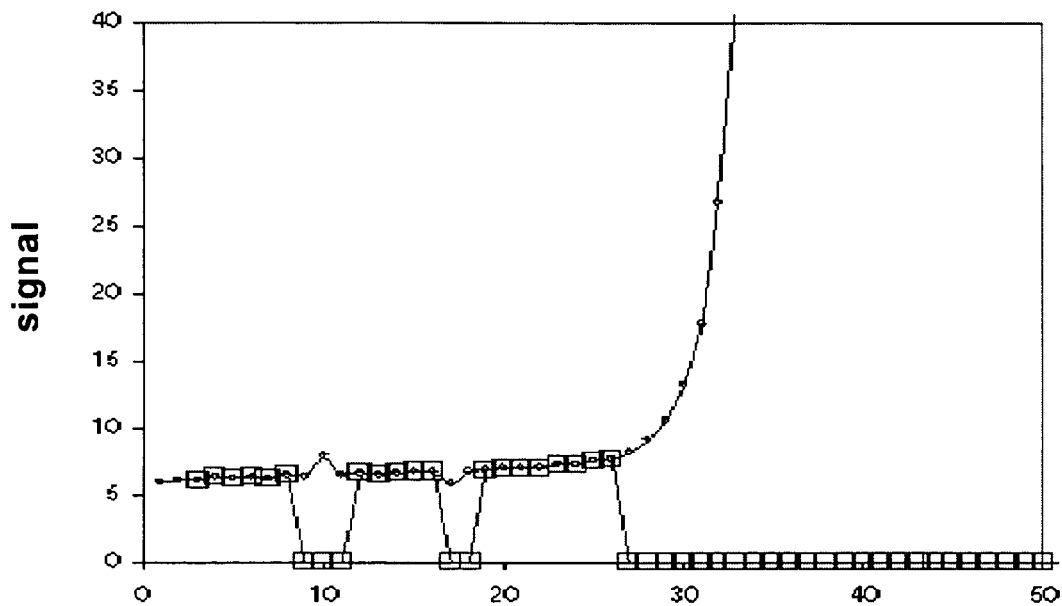
FIGS. 15A-B show growth curves with baseline slope anomalies and indicates with a box the data points to be used in determining a baseline for calculation of the elbow value.
Figure 15B:
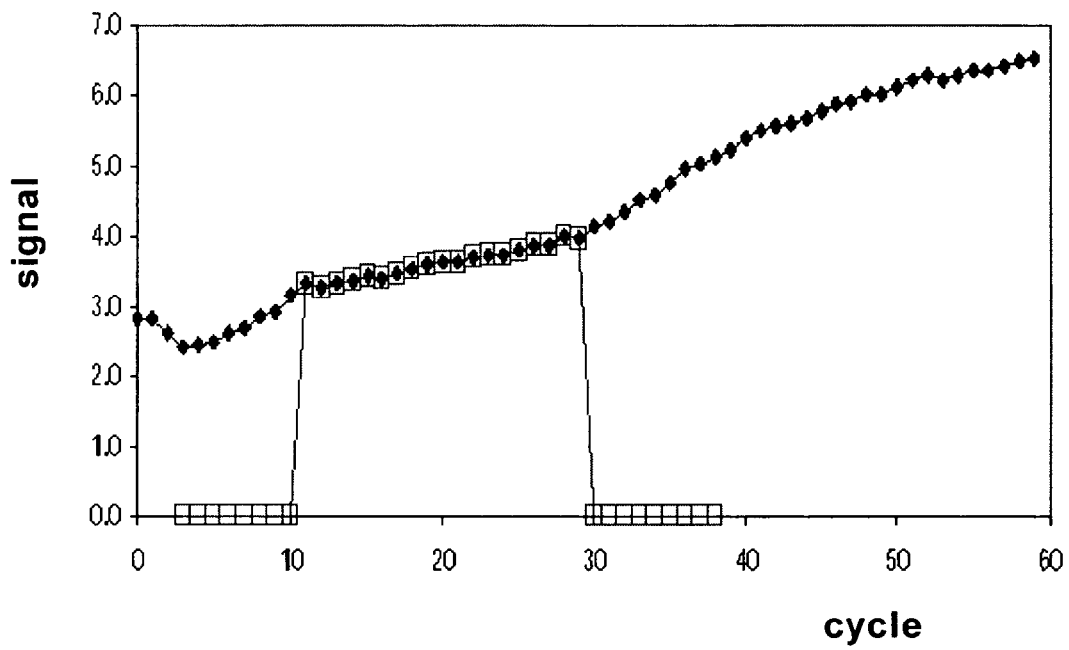

FIGS. 15A & B show two growth curves with the acceptable baseline points in boxes. For the curve in FIG. 15A, five points that form two separate spikes (at cycles 9-11 and 17-18) are excluded from the set of points used to calculate the baseline; for the curve in FIG. 15B, eight initial points (at cycles 3-10) are excluded. The data to be included in the analysis can be truncated. For example, data beyond a specified cycle number can be excluded, or data can be excluded once a certain total number of valid baseline points have been identified.

Linear regression is performed on valid baseline points. As described previously and provided in equations (4-5), the regression yields the BLslope and BLintercept, which can be used to normalize the data. The normalized growth curve has a baseline that begins at about 0.0 and then increases.

The point where the normalized growth curve crosses (ASV-1) is the elbow value. The elbow value can be calculated, for example, using a two-point linear interpolation as given previously, or using a two-point logarithmic interpolation defined as:

$$n_{ASV} = n_{lo} + \frac{\log[(Y_{ASV})/(Y_{lo})]}{\log[(Y_{hi})/(Y_{lo})]} * (n_{hi} - n_{lo}) \quad (21)$$

An exemplary method for performing multicomponent analysis (step 704, above) is as follows.

The pairs of fluorescent dyes that are used to detect each nucleic acid may have overlapping spectra (excitation/emission), at least in part because filter systems and fluorescent dyes do not perfectly match. This overlap in spectra is characterized as "crosstalk." Typically, there are four dyes, two for the target nucleic acid and two for the standard. Multicomponent analysis can extract a reliable signal measure from the potentially overlapping measurements.

For example, for m equations and n unknown dye concentrations, assuming that m≧n, the signals or concentrations are:

$$c = (A^T \cdot A)^{31\ 1} \cdot A^T (f - b) \quad (22)$$

where A is the assay-specific crosstalk matrix obtained from the test file (an m×n matrix), f includes the four fluorescent readings obtained during data acquisition from each of the 4 filter combinations (a 1×4 vector), b is the blank (a 1×4 vector), and c is the crosstalk-corrected signal data or dye concentrations (a 1×m vector). The crosstalk matrix A will typically be at least a 4×4 matrix. The size of the matrix is determined by the number of filter combinations that are used, and will be larger if more filter combinations are used.

Because the multicomponent analysis needs to be done after every cycle, the cost of multicomponent analysis should be minimized. For example, a matrix B can be pre-calculated:

$$B = (A^T \cdot A)^{-1} \cdot A^T \quad (23)$$

and then the equation $$c = B(f - b)$$

can be used at each step to determine dye concentration.

The invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. The essential elements of a computer are a processor for executing instructions and a memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented on a computer system having a display device such as a monitor or LCD screen for displaying information to the user and a keyboard and a pointing device such as a mouse or a trackball by which the user can provide input to the computer system. The computer system can be programmed to provide a graphical user interface through which computer programs interact with users.

A number of embodiments of the invention have been described. Nevertheless, it will be understood that various modifications may be made without departing from the spirit and scope of the invention. For example, while the techniques are described as including the generation of a growth curve from the signal data, it may not be necessary to actually plot a growth curve to perform the techniques of the invention. Separate amplifications can be used. Other algorithms for identifying growth curve values can be used to generate the data used to calibrate nucleic acids and quantitate a target nucleic acid. Calibration equations having different forms and parameters can be used. Accordingly, other embodiments are within the scope of the following claims.

What is claimed is:

1. A method for determining an amount of a target nucleic acid in a sample, comprising:
generating signal data by performing a plurality of cycles of amplification on a target nucleic acid and a standard nucleic acid, the signal data including a series of standard signal values indicative of a quantity of the standard nucleic acid present during cycles of the standard amplification, and a series of target signal values indicative of a quantity of the target nucleic acid present during cycles of the target amplification;
defining a target growth curve value using the target signal values and a standard growth curve value using the standard signal values, said defining comprising determining an elbow value for the standard nucleic acid or the target nucleic acid, wherein determining an elbow value includes interpolating between a number of a cycle for which the standard or target signal, respectively, is less than the predefined signal value and a number of a cycle for which the standard or target signal, respectively, is greater than the predefined signal value; and
outputting a quantity indicative of an initial amount of the target nucleic acid according to a calculation that comprises use of a calibration equation, where the calibration equation is a nonlinear equation, wherein the calibration equation expresses quantity of target nucleic acid as a function of quantity of standard nucleic acid and difference in cycle numbers for standard and target nucleic acid, wherein the calculation comprises use of an initial amount of the standard nucleic acid for the quantity of the standard nucleic acid in the calibration equation and use of difference in the growth curve elbow values for the standard and target nucleic acid for the difference in the cycle numbers for the standard and target nucleic acid in the calibration equation to determine the initial amount of the target nucleic acid.

2. The method of claim 1, further comprising:
checking the target signal values or the standard signal values for a dip, spike, drift, or step and adjusting the target signal values or standard signal values, respectively.

3. The method of claim 2, wherein:
adjusting the target signal values or standard signal values includes reporting that data is inadequate for calculating an initial amount of the target nucleic acid.

4. The method of claim 2, wherein:
adjusting the target signal values or standard signal values includes deleting data values corresponding to the dip, spike, drift, or step.

5. The method of claim 1, wherein defining a target growth curve value using the target signal values and a standard growth curve value using the standard signal values includes:
defining a baseline for a standard or target growth curve using a subset of the standard signal values or a subset of the target growth curve values, respectively; and
normalizing the corresponding signal data with respect to the baseline.

6. The method of claim 5, wherein defining a baseline includes:
identifying one or more dips or spikes in the signal data; and
excluding one or more data value corresponding to the one or more dips or spikes from a set of data to be used to define the baseline.

7. The method of claim 6, wherein identifying one or more spikes includes:
identifying a first order differences between adjacent data points and two or more second order differences for the adjacent data points; and
confirming a spike if there is a first difference larger than a predefined SPAMP value and a change in sign of the second-order differences.

8. The method of claim 1, wherein:
determining an elbow value for the standard nucleic acid or the target nucleic acid includes determining a cycle of the standard or target amplification where the standard or target signal has a predefined signal value.

9. The method of claim 1, wherein:
determining an elbow value for the standard nucleic acid or the target nucleic acid includes determining a standard elbow value for the standard nucleic acid and a target elbow value for the target nucleic acid.

10. The method of claim 1, wherein:
determining an elbow value includes determining the elbow value from the respective standard or target growth curve.

11. The method of claim 1, wherein:
the elbow value is a fractional cycle number.

12. The method of claim 1, wherein:
the calibration equation is derived from target growth curve values and standard growth curve values from a series of amplification experiments performed on known quantities of the target nucleic acid and a known quantity of the standard nucleic acid.

13. The method of claim 12, wherein:
the calibration equation relates the initial amount of the target nucleic acid to the known quantity of the standard nucleic acid using the target and standard growth curve values.

14. The method of claim 13, wherein the calibration equation is defined by:
plotting a correlate of the initial amount of the target nucleic acid against a function of the known quantity of the standard nucleic acid and the target and standard growth curve values to produce a calibration plot; and
fitting a curve to the calibration plot.

15. The method of claim 14, wherein:
the function of the known quantity of the standard nucleic acid and the target and standard growth curve values is a function of the difference between the target and standard growth curve values.

16. The method of claim 15, wherein:
fitting a curve to the calibration plot includes fitting a second-order nonlinear curve to the calibration plot.

17. The method of claim 16, wherein:
the nonlinear curve is defined by the formula:

$$T_o = Q_o 10^{a(n_Q - n_T)^2 + b(n_Q - n_T) + c},$$

where $T_o$ is the initial amount of the target nucleic acid, $Q_o$ is the initial amount of the standard nucleic acid, $n_Q$ is the cycle number at which the quantity of standard nucleic acid is Q, and $n_T$ is the cycle number at which the quantity of standard is T.

18. The method of claim 1, wherein said interpolating comprises a two-point linear interpolation.

19. The method of claim 1, wherein said interpolating comprises a two-point logarithm interpolation.

20. A method for determining an amount of a target nucleic acid in a sample, comprising:
amplifying a known quantity of a standard nucleic acid and a sample of the target nucleic acid in successive cycles of a standard amplification and a target amplification, respectively; monitoring a standard signal that is indicative of a quantity of the standard nucleic acid and a target signal that is indicative of a quantity of the target nucleic acid to produce standard growth data and target growth data;
defining a standard value from the standard growth data characterizing the standard amplification and a target value from the target growth data characterizing the target amplification, said defining comprising determining an elbow value for the standard nucleic acid or the target nucleic acid, wherein determining an elbow value includes interpolating between a number of a cycle for which the standard or target signal, respectively, is less than the predefined signal value and a number of a cycle for which the standard or target signal, respectively, is greater than the predefined signal value; and
determining a quantity indicative of the amount of the target nucleic acid using a nonlinear calibration equation and parameters for the calibration equation that relate a quantity of the target nucleic acid to the known quantity of the standard nucleic acid using the target and the standard values.

21. The method of claim 20, wherein amplifying a known quantity of a standard nucleic acid and a sample of the target nucleic acid includes:
combining the known quantity of a standard nucleic acid and the sample of the target nucleic acid to form a mixture; and
co-amplifying the standard nucleic acid and the target nucleic acid in the mixture.

22. The method of claim 21, wherein:
co-amplifying the standard nucleic acid and the target nucleic acid includes using a common pair of primers.

23. The method of claim 21, wherein:
the standard signal is a first fluorescence signal and the target signal is a second fluorescence signal.

24. The method of claim 23, wherein:
monitoring a standard signal or a target signal includes monitoring a fluorescence signal derived from one of a pair of fluorescent dyes.

25. The method of claim 21, wherein:
monitoring the standard or target signal includes monitoring the annealing of an oligonucleotide probe to the interior of the standard or target nucleic acid, respectively.

26. The method of claim 20, wherein said interpolating comprises a two-point linear interpolation.

27. The method of claim 20, wherein said interpolating comprises a two-point logarithm interpolation.

28. The method of claim 20, wherein the calibration equation is defined by producing a calibration plot of the ratio of the initial amount of the target nucleic acid to the known quantity of the standard nucleic acid against the difference between the target and standard growth curve values and fitting a second-order nonlinear curve to the calibration plot, wherein the nonlinear curve is defined by the equation: $T_o = Q_o 10^{a(n_Q - n_T)^2 + b(n_Q - n_T) + c}$, where $T_o$ is the initial amount of the target nucleic acid, $Q_o$ is the initial amount of the standard nucleic acid, $n_Q$ is the cycle number at which the quantity of standard nucleic acid is Q, and $n_T$ is the cycle number at which the quantity of standard is T.

29. A method for determining an amount of a target nucleic acid in a sample, comprising:
generating signal data by performing a plurality of cycles of amplification on a target nucleic acid and a standard nucleic acid, the signal data including a series of standard signal values indicative of quantities of the standard nucleic acid present during cycles of the standard amplification, and a series of target signal values indicative of quantities of the target nucleic acid present during cycles of the target amplification;
checking the target signal values and the standard signal values for an anomaly and adjusting the target signal values and standard signal values to account for the anomaly;

defining a target growth curve value using the target signal values and a standard growth curve value using the standard signal values, said defining comprising determining an elbow value for the standard nucleic acid or the target nucleic acid, wherein determining an elbow value includes interpolating between a number of a cycle for which the standard or target signal, respectively, is less than the predefined signal value and a number of a cycle for which the standard or target signal, respectively, is greater than the predefined signal value; and outputting a quantity indicative of an amount of the target nucleic acid using the target and the standard growth curve elbow values, wherein the quantity is determined according to a calculation that comprises use of a calibration equation, where the calibration equation is a nonlinear equation, wherein the calibration equation expresses quantity of target nucleic acid as a function of quantity of standard nucleic acid and difference in cycle numbers for standard and target nucleic acid, wherein the calculation comprises use of an initial amount of the standard nucleic acid for the quantity of the standard nucleic acid in the calibration equation and use of difference in the growth curve elbow values for the standard and target nucleic acid for the difference in the cycle numbers for the standard and target nucleic acid in the calibration equation to determine the initial amount of the target nucleic acid.

30. The method of claim 29, wherein:

the anomaly is a dip, spike, step or drift.

31. A computer program product, tangibly stored on a computer-readable medium, for determining an amount of a target nucleic acid in a sample, comprising instructions operable to cause a programmable processor to:

receive signal data for a plurality of cycles of amplification performed on a target nucleic acid and a standard nucleic acid, the signal data including a series of standard signal values indicative of a quantity of the standard nucleic acid present during cycles of the standard amplification, and a series of target signal values indicative of a quantity of the target nucleic acid present during cycles of the target amplification;

define a target growth curve value using the target signal values and a standard growth curve value using the standard signal values, said defining comprising determining an elbow value for the standard nucleic acid or the target nucleic acid, wherein determining an elbow value includes interpolating between a number of a cycle for which the standard or target signal, respectively, is less than the predefined signal value and a number of a cycle for which the standard or target signal, respectively, is greater than the predefined signal value; and output an initial amount of the target nucleic acid according to a calculation that comprises use of a calibration equation, where the calibration equation is a nonlinear equation, wherein the calibration equation expresses quantity of target nucleic acid as a function of quantity of standard nucleic acid and difference in cycle numbers for standard and target nucleic acid, wherein the calculation comprises use of an initial amount of the standard nucleic acid for the quantity of the standard nucleic acid in the calibration equation and use of difference in the growth curve elbow values for the standard and target nucleic acid for the difference in the cycle numbers for the standard and target nucleic acid in the calibration equation to determine the initial amount of the target nucleic acid.

32. A computer program product, tangibly stored on a computer-readable medium, for determining an amount of a target nucleic acid in a sample, comprising instructions operable to cause a programmable processor to:

receive signal data for a plurality of cycles of amplification performed on a target nucleic acid and a standard nucleic acid, the signal data including a series of standard signal values indicative of quantities of the standard nucleic acid present during cycles of the standard amplification, and a series of target signal values indicative of quantities of the target nucleic acid present during cycles of the target amplification;

check the target signal values and the standard signal values for an anomaly and adjusting the target signal values and standard signal values to account for the anomaly;

define a target growth curve value using the target signal values and a standard growth curve value using the standard signal values, said defining comprising determining an elbow value for the standard nucleic acid or the target nucleic acid, wherein determining an elbow value includes interpolating between a number of a cycle for which the standard or target signal, respectively, is less than the predefined signal value and a number of a cycle for which the standard or target signal, respectively, is greater than the predefined signal value; and output a calculated amount indicative of the target nucleic acid using the target and the standard growth curve values, wherein the quantity is determined according to a calculation that comprises use of a calibration equation, where the calibration equation is a nonlinear equation, wherein the calibration equation expresses quantity of target nucleic acid as a function of quantity of standard nucleic acid and difference in cycle numbers for standard and target nucleic acid, wherein the calculation comprises use of an initial amount of the standard nucleic acid for the quantity of the standard nucleic acid in the calibration equation and use of difference in the growth curve elbow values for the standard and target nucleic acid for the difference in the cycle numbers for the standard and target nucleic acid in the calibration equation to determine the initial amount of the target nucleic acid.

33. A computer-implemented system for determining an amount of a target nucleic acid in a sample, comprising:

means for receiving signal data for a plurality of cycles of amplification performed on a target nucleic acid and a standard nucleic acid, the signal data including a series of standard signal values indicative of a quantity of the standard nucleic acid present during cycles of the standard amplification, and a series of target signal values indicative of a quantity of the target nucleic acid present during cycles of the target amplification;

means for defining a target growth curve value using the target signal values and a standard growth curve value using the standard signal values, said defining comprising determining an elbow value for the standard nucleic acid or the target nucleic acid, wherein determining an elbow value includes interpolating between a number of a cycle for which the standard or target signal, respectively, is less than the predefined signal value and a number of a cycle for which the standard or target signal, respectively, is greater than the predefined signal value;

means for calculating an initial amount of the target nucleic acid according to a calibration equation, wherein the calibration equation is a nonlinear equation, wherein the calibration equation expresses quantity of target nucleic acid as a function of quantity of standard nucleic acid and difference in cycle numbers for standard and target nucleic acid, wherein the calculation comprises use of an initial amount of the standard nucleic acid for the quantity of the standard nucleic acid in the calibration equation and use of difference in the growth curve elbow values for the standard and target nucleic acid for the difference in the cycle numbers for the standard and target nucleic acid in the calibration equation to determine the initial amount of the target nucleic acid; and means for providing an output of the calculated initial amount indicative of the target nucleic acid.

* * * * *

UNITED STATES PATENT AND TRADEMARK OFFICE
CERTIFICATE OF CORRECTION

PATENT NO. : 7,788,039 B2  
APPLICATION NO. : 10/946904  
DATED : August 31, 2010  
INVENTOR(S) : Thomas Vess It is certified that error appears in the above-identified patent and that said Letters Patent is hereby corrected as shown below:

Title Page, Item [56] References Cited, Other Publications, Quondam reference, please delete "*crassa*" and insert --*Crassa*-- therefor;

Column 23, line 42 (Claim 17), please delete "$T_o = Q_o 10^{a(nQ - nT)^2 + b(nQ - nT) + c}$" and insert -- $T_o = Q_o 10^{a(n_Q - n_T)^2 + b(n_Q - n_T) + c}$ -- therefor;

Column 23, line 46 (Claim 17), after "standard" please insert --nucleic acid--;

Column 24, line 47-48 (Claim 28), please delete "$T_o = Q_o 10^{a(nQ - nT)^2 + b(nQ - nT) + c}$" and insert -- $T_o = Q_o 10^{a(n_Q - n_T)^2 + b(n_Q - n_T) + c}$ -- therefor;

Column 24, line 52 (Claim 28), after "standard" please insert --nucleic acid--.

Signed and Sealed this

Seventh Day of December, 2010

David J. Kappos  
*Director of the United States Patent and Trademark Office*